United States Patent [19]

Rideout et al.

[11] Patent Number: 5,153,318
[45] Date of Patent: Oct. 6, 1992

[54] 3'-AZIDO NUCLEOSIDE COMPOUND

[75] Inventors: Janet L. Rideout; George A. Freeman, both of Raleigh; Steven A. Short, Cary; Merrick R. Almond, Apex, all of N.C.; Jon L. Collins, Bloomington, Ind.

[73] Assignee: Burroughs Wellcome Co., N.C.

[21] Appl. No.: 591,916

[22] Filed: Oct. 2, 1990

[30] Foreign Application Priority Data

Oct. 3, 1989 [GB] United Kingdom ............... 8922285
Jul. 31, 1990 [GB] United Kingdom ............... 9016775

[51] Int. Cl.$^5$ .......................................... C07H 19/00
[52] U.S. Cl. ....................................... 536/24; 536/26
[58] Field of Search ................... 536/24, 26; 514/45, 514/46

[56] References Cited

U.S. PATENT DOCUMENTS

| | | | |
|---|---|---|---|
| 3,929,764 | 12/1975 | Fauland et al. | 536/26 |
| 3,983,104 | 9/1976 | Vorbruggen | 536/24 |
| 4,724,232 | 2/1988 | Rideout et al. | 514/50 |
| 4,880,782 | 11/1989 | Eckstein et al. | 514/45 |

FOREIGN PATENT DOCUMENTS

| | | |
|---|---|---|
| 0217580A2 | 4/1987 | European Pat. Off. |
| 0285432A2 | 10/1988 | European Pat. Off. |
| 0286825A2 | 10/1988 | European Pat. Off. |
| 0294114A2 | 12/1988 | European Pat. Off. |
| 0352248 | 1/1990 | European Pat. Off. ............. 536/26 |
| 0362967A1 | 4/1990 | European Pat. Off. |

OTHER PUBLICATIONS

E. M. Southern, J. Mol. Biol., (1975), 98, pp. 503-517, Detection of Specific Sequences Among DNA Fragments Separated by Gel Electrophoresis.

Mary Ann Sells, et al., Journal of Virology, Aug., 1988, vol. 62, No. 8, pp. 2836-2844, Replicative Intermediates of Hepatitis B Virus in HepG2 Cells that Produce Infectious Virions.

George W. J. Fleet, et al., Tetrahedron Letters, 1987, vol. 28, No. 31, pp. 3615-3618, Methyl 5-0-Tert-Butyl-diphenylsilyl-2-Deoxy-D-Threo-Pentofuranoside; An Approach to the Synthesis of 3'-Substituted-2',-3'-Dideoxynucleosides Including 3'-Azido-3'-Deoxy-thymidine and of 3'-Substituted-2',3'-Dideoxy-C-Nucleosides.

Robert W. McCollum, Viral Hepatitis, Chapter 12, pp. 327-350.

Jan S. Tuttleman, et al., Journal of Virology, Apr., 1986, vol. 58, No. 1, pp. 17-25, In Vitro Experimental Infection of Primary Duck Hepatocyte Cultures with Duck Hepatitis B Virus.

M. Imazawa, et al., J. Org. Chem., 1978, vol. 43, No. 15, Synthesis of 3'-Azido-2',3'-dideoxyribofuranosylpurines.

Ruiming Zou, et al., Communications, Jan. 6, 1987, pp. 1436-1437.

R. Cardinaud, Pyrimidine Metabolizing Enzymes, [60], pp. 446-455, 1987.

Primary Examiner—Johnnie R. Brown
Assistant Examiner—J. Oliver Wilson
Attorney, Agent, or Firm—Donald Brown; Hannah O. Green; Lawrence A. Nielsen

[57] ABSTRACT

The present invention relates to 3'-azido purine nucleosides and their use in medical therapy, particularly for the treatment of human immunodeficiency virus and hepatitis B virus infections, to methods for their preparation and to compositions containing them.

2 Claims, No Drawings

3'-AZIDO NUCLEOSIDE COMPOUND

The present invention relates to 3'-azido purine nucleosides and pharmaceutically acceptable derivatives thereof, and their use in therapy, particularly for the treatment of certain viral infections.

One group of viruses which has recently assumed a particular importance are the retroviruses. Retroviruses form a sub-group of RNA viruses which, in order to replicate, must first "reverse transcribe" the RNA of their genome into DNA ("transcription" conventionally describes the synthesis of RNA from DNA). Once in the form of DNA, the viral genome may be incorporated into the host cell genome, allowing it to take full advantage of the host cell's transcription/translation machinery for the purposes of replication. Once incorporated the viral DNA is virtually indistinguishable from the host's DNA and, in this state, the virus may persist for as long as the cell lives. As it is virtually invulnerable to attack in this form, any treatment must be directed at another stage of the virus life cycle.

A species of retrovirus, human immunodeficiency virus (HIV), has been reproducibly isolated from patients with acquired immune deficiency syndrome (AIDS) or with the symptoms that frequently precede AIDS.

AIDS is an immunosuppressive or immunodestructive disease that predisposes subjects to fatal opportunistic infections. Characteristically, AIDS is associated with a progressive depletion of T-cells, especially the helper-inducer subset bearing the OKT4 surface marker. HIV is cytopathic and appears to preferentially infect and destroy T-cells bearing the OKT4 marker, and it is now generally recognized that HIV is the etiological agent of AIDS.

Since the discovery that HIV is the etiological agent of AIDS, numerous proposals have been made for anti-HIV chemotherapeutic agents that may be effective in treating AIDS. Thus, for example, U.S. Pat. No. 4,724,232 describes 3'-azido-3'-deoxythymidine (which has the approved name zidovudine) its pharmaceutically acceptable derivatives and their use in the treatment of human retrovirus infections including AIDS and associated clinical conditions. Further 3'-azido nucleoside analogues are described in European Patent Specifications 217580 and 362967 and U.S. Pat. No. 4,880,782.

Another group of viral pathogens of major consequence worldwide are the hepatitis viruses, in particular hepatitis B virus (HBV).

HBV is most common in Asian countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease. The United States currently contains an estimated pool of 500,000–1 million infectious carriers. Chronic active hepatitis will develop in over 25% of carriers and often progresses to cirrhosis. It is estimated that 5000 people die from HBV related cirrhosis each year in the U.S.A. and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as lined above. In "Viral Infections of Humans" (second edition, Ed., Evans, A. S. (1982) Plenum Publishing Corporation, New York), Chapter 12 describes in detail, the etiology of viral hepatitis infections.

We have now discovered that certain 3'-azido purine nucleosides as referred to below are useful for the of viral infections, particularly retroviral infections, especial or hepatitis viral infections, particularly HBV.

According to the present invention therefore we provide a compound of formula (I):

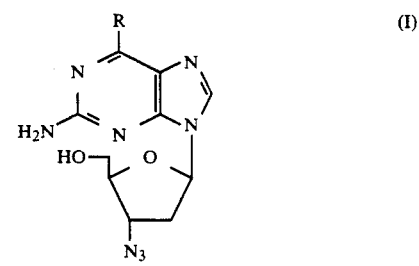
(I)

wherein R represents halogen (e.g., chlorine); $C_{1-6}$ alkoxy (e.g. methoxy or isopropoxy); $C_{3-6}$ cycloalkyloxy (e.g. cyclobutoxy, cyclopropyloxy); aryloxy (e.g. phenyloxy) or arylalkoxy (e.g. benzyloxy) in which the aryl may optionally be substituted with $C_{1-6}$ alkyl, $C_{1-6}$ alkoxy, halogen, nitro or hydroxyl; amino which is substituted by one or two substituents independently selected from $C_{1-6}$ alkyl (e.g. methyl), aryl (e.g. phenyl), aralkyl including aracycloalkyl (e.g. benzyl, phenylethyl, phenylcyclopropyl) and $C_{3-6}$ cycloalkyl (e.g. cyclopropyl); or a 4- to 6- membered heterocyclic ring containing at least one nitrogen atom (e.g. azetidinyl, pyrrolidinyl or piperidinyl) which ring is bonded to the purine base via a/the nitrogen atom; or a pharmaceutically acceptable derivative thereof.

Compounds of formula (I) above and their pharmaceutically acceptable derivatives include compounds of formula (IA).

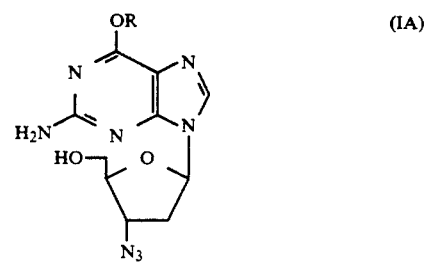
(IA)

wherein R represents a $C_{1-6}$ straight chain, branched chain or cyclic alkyl (e.g. methyl) group or a pharmaceutically acceptable derivative thereof.

Compounds of formula (I) above and their pharmaceutically acceptable derivatives include compounds of formula (IB)

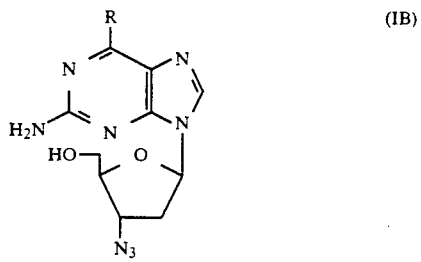

wherein R represents halogen (e.g. chlorine); $C_{1-6}$ alkoxy (e.g. methoxy or isopropoxy); $C_{3-6}$ cycloalkyloxy (e.g. cyclopropyloxy); aryloxy (e.g. phenyloxy) or arylalkoxy (e.g. benzyloxy) in which the aryl may optionally be substituted with $C_{1-6}$ alkyl, $C_{1-6}$ alkoxy, halogen, nitro or hydroxyl; amino which is substituted by one or two substitutients independently selected from $C_{1-6}$ alkyl (e.g. methyl), aryl (e.g. phenyl), aralkyl (e.g. benzyl) and $C_{3-6}$ cycloalkyl (e.g. cyclopropyl); or a pharmaceutically acceptable derivative thereof.

Preferred compounds of formula (I) include those wherein R represents halogen (e g chlorine); $C_{1-6}$ alkoxy (e.g. methoxy, isopropoxy); $C_{3-6}$ cycloalkyloxy (e.g. cyclobutoxy); aryloxy (e.g. phenyloxy); arylalkoxy (e.g. benzyloxy); amino which is substituted by one or two substituents independently selected from $C_{1-6}$ alkyl (e.g. methyl, propyl), aralkyl including aracycloalkyl (e.g. benzyl, phenylethyl, phenylcyclopropyl) or a 4- or 5- membered heterocyclic ring containing a nitrogen atom (e.g. azetidinyl, pyrrolidinyl) which ring is bonded to the purine base via the nitrogen atom or a pharmaceutically acceptable derivative thereof.

Particularly preferred compounds of formula (I) include those wherein R represents $C_{1-6}$ alkoxy (e.g. methoxy, isopropoxy); aryloxy (e.g. phenyloxy), arylalkoxy (e.g. benzyloxy); amino which is substituted by one or two substitutents independently selected from $C_{1-6}$ alkyl (e.g. methyl or propyl) and $C_{3-6}$ cycloalkyl (e.g. cyclopropyl); or a 4- or 5-membered heterocyclic ring containing a nitrogen atom (e.g. azetidinyl, pyrrolidinyl) which ring is bonded to the purine base via the nitrogen atom or a pharmaceutically acceptable derivative.

Examples of especially preferred compounds of formula (I) are:

1. 2-amino-9-(3-azido-2,3-dideoxy-$\beta$-D-erythro-pentofuranosyl)-6-methoxy-9H-purine,
2. 2-amino-9-(3-azido-2,3-dideoxy-$\beta$-D-erythro-pentofuranosyl)-6-benzyloxy-9H-purine,
3. 2-amino-9-(3-azido-2,3-dideoxy-$\beta$-D-erythro-pentofuranosyl)-6-dimethylamino-9H-purine,
4. 2-amino-9-(3-azido-2,3-dideoxy-$\beta$-D-erythro-pentofuranosyl)-6-propylamino-9H-purine,
5. 2-amino-9-(3-azido-2,3-dideoxy-$\beta$-D-erythro-pentofuranosyl)-6-(cyclopropylmethylamino)-9H-purine,
6. 2-amino-9-(3-azido-2,3-dideoxy-$\beta$-D-erythro-pentofuranosyl)-6-phenoxy-9H-purine.
7. 2-amino-6-(1-azetidinyl)-9-(3-azido-2,3-dideoxy-$\beta$-D-erythropentofuranosyl)-9H-purine.
8. 2-amino-9-(3-azido-2,3-dideoxy-$\beta$-D-erythro-pentofuranosyl)-6-pyrrolidinyl-9H-purine.

Compounds numbered 1 to 6 are especially useful for the treatment of HBV infections. Compounds numbered 2, 3 and 5 are particularly useful for the treatment of HIV infections.

The compounds of formula (I) above and their pharmaceutically acceptable derivatives are hereinafter referred to as the compounds according to the invention.

In one aspect of the invention there are provided the compounds according to the invention for use in medical therapy particularly for the treatment of retroviral or hepatitis infections.

Examples of retroviral infections which may be treated or prevented in accordance with the invention include human retroviral infections such as Human Immunodeficiency Virus (HIV) e.g. HIV-1 or HIV-2 and Human T-cell Lymphotropic Virus (HLTV) e.g. HTLV-I or HTLV-II infections. The compounds according to the invention are especially useful for the treatment of AIDS and related clinical conditions such as AIDS-related complex (ARC), progressive generalized lymphadenopathy (PGL), AIDS-related neurological conditions such as multiple sclerosis or tropical paraperesis and also anti-HIV antibody-positive and HIV-positive conditions including such conditions in asymptomatic patients, Kaposi's sarcoma and thrombocytopenic purpura.

An example of a hepatitis infection which may be treated or prevented in accordance with the invention is a hepatitis B infection.

The compounds according to the invention may also be used in the treatment of psoriasis.

In a further aspect of the present invention there is included:

a) A method for the treatment of a viral infection, particularly a hepatitis or retroviral infection in a subject, e.g. a mammal such as man which comprises treating the subject with a therapeutically effective amount of a compound according to the invention.

b) Use of a compound according to the invention in the manufacture of a medicament for the treatment of any of the above-mentioned infections or conditions.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) the said compound or an antivirally active metabolite or residue thereof.

Preferred esters include carboxylic acid esters in which the non-carbonyl moiety of the carboxylic acid portion of the ester grouping is selected from straight or branched chain alkyl e.g. methyl, ethyl, n-propyl i-propyl, t-butyl, n-butyl, alkoxyalkyl (e.g. methoxymethyl), arylalkyl (e.g. benzyl), aryloxyalkyl (e.g. phenoxymethyl), aryl (e.g. phenyl optionally substituted by halgen, $C_{1-4}$ alkyl or alkoxy); sulfonate esters such as alkyl- or arylalkylsulfonyl (e.g. methanesulfonyl); amino acid esters (e.g. L-valyl or L-isoleucyl); and 5'- mono- di- or tri-phosphate esters. The phosphate esters may be further esterified by, for example, a $C_{1-20}$ alcohol or reactive derivative thereof, or by a 2,3- di($C_{6-24}$)acyl glycerol.

With regard to the above-described esters unless otherwise specified, any alkyl moiety present advantageously contains 1 to 18 carbon atoms, particularly 1 to 4 carbon atoms. Any aryl moiety present in such esters advantageously comprises a phenyl group.

Any reference to any of the above compounds also includes a reference to a pharmaceutically acceptable salt thereof.

Examples of pharmaceutically acceptable salts according to the invention and pharmaceutically acceptable derivatives thereof include base salts. e.g. derived form an appropriate base, such as alkali metal (e.g. sodium), alkaline earth metal (e.g. magnesium) salts, ammonium and $NX_4^+$ (wherein X is $C_{1-4}$ alkyl). Pharmaceutically acceptable acid addition salts include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The above compounds according to the invention and their pharmaceutically acceptable derivatives may be employed in combination with other therapeutic agents for the treatment of the above infections or conditions. Examples of such further therapeutic agents include agents that are effective for the treatment of HIV infections, HBV infections or associated conditions such as 3'-azido-3'-deoxythymidine (zidovudine), other 2',3'-dideoxynucleosides such as 2',3'-dideoxycytidine, 2',3'-dideoxyadenosine and 2',3'-dideoxyinosine, carbovir, acyclic nucleosides (e.g. acyclovir) 3'-deoxy-2',3'-didehydrothymidine (D4T), 3'-thia-2',3'-dideoxycytidine, interferons such as α-interferon, renal excretion inhibitors such as probenicid, nucleoside transport inhibitors such as dipyridamole, as well as immunomodulators such as interleukin II and granulocyte macrophage colony stimulating factors, soluble $CD_4$ or genetically engineered derivatives thereof, compounds which affect cellular membranes such as calcium channel inhibitors e.g. verapamil, TIBO, and phosphonoformic acid. The component compounds of such combination therapy may be administered simultaneously, in either separate or combined formulations, or at different times e.g. sequentially such that a combined effect is achieved.

The present invention further provides pharmaceutical formulations of the compounds according to the invention, also referred to herein as active ingredients, which may be administered for therapy by any suitable route including oral, rectal, nasal, topical (including buccal and sublingual), vaginal and parenteral (including subcutaneous, intramuscular, intravenous and intradermal). It will also be appreciated that the preferred route will vary with the condition and age of the recipient, the nature of the infection and the chosen active ingredient.

In general a suitable dose of the active ingredient for the treatment of the above-mentioned viral infections, e.g. HIV-1 and HBV infections, will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 $\mu M$, preferably about 2 to 50 $\mu M$, most preferably about 3 to about 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprises at least one active ingredient, as defined above, together with one or more acceptable carriers thereof and optionally other therapeutic agents. Each carrier must be "acceptable" in the sense of being compatible with the other ingredients of the formulation and not injurious to the patient.

Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach. This is particularly advantageous for purine nucleoside derivatives as such compounds are susceptible to acid hydrolysis.

Formulations suitable for oral use as described above may also include buffering agents designed to neutralize stomach acidity. Such buffers may be chosen from a variety of organic or inorganic agents such as weak acids or bases admixed with their conjugated salts.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels pastes, foams or spray formulations containing in addition to the active ingredient such carriers as are known in the art to be appropriate.

Formulations suitable for parenteral administration include aqueous and non-aqueous isotonic sterile injections solutions which may contain anti-oxidants, buffers, bacteriostats and solutes which render the formulation isotonic with the blood of the intended recipient; and aqueous and non-aqueous sterile suspensions which may include suspending agents and thickening agents, as liposomes or other microparticulate systems which are designed to target the compounds to blood components or one or more organs. The formulations may be presented in unit-dose or multi-dose sealed containers, for example, ampules and vials and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The compounds according to the invention may also be presented for the use in the form of veterinary formulations, which may be prepared, for example, by methods that are conventional in the art.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes a process for the preparation of the compound of formula (I) and pharmaceutically acceptable derivatives thereof which comprises either:

A) removal of a hydroxy protecting group Y from a compound of formula (II)

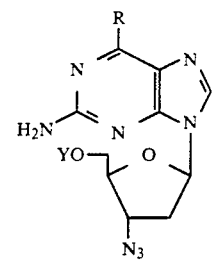

(II)

(wherein R is as hereinbefore defined and Y represents a hydroxy protecting group); or B) reacting a compound of formula (IIA)

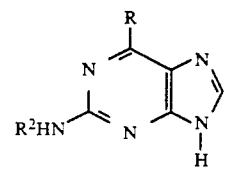

(IIA)

(wherein R is as hereinbefore defined, $R^2$ is an amino protecting group), or a functional equivalent thereof, for example a silylated derivative thereof, with a compound of formula (IIB)

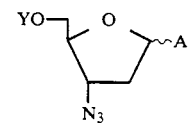

(IIB)

(wherein Y is as defined above, A is a leaving group) to form a compound of formula (IIC)

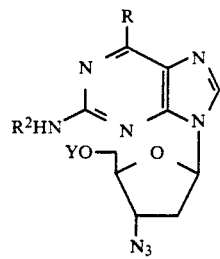

(IIC)

wherein R, $R^2$ and Y are as defined above, and thereafter deprotecting the amino and hydroxy groups; or C) reacting a compound of formula (IID)

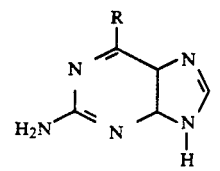

(IID)

(wherein R is as hereinbefore defined) with a compound of formula (IIE)

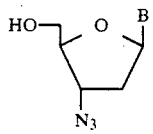

(wherein B represents a pyrimidine or purine base) in the presence of an appropriate transferase enzyme;

D) reaction of a compound of formula (I) wherein R represents halogen with an appropriate agent serving to convert the said halogen to an alternative group represented by R in formula (I); and thereafter, or simultaneously therewith, effecting one or more of the following optional conversions:
(i) removing any remaining protecting group(s);
(ii) when a compound of formula (I) is formed, converting the said compound into a pharmaceutically acceptable derivative thereof; and
(iii) when a pharmaceutically acceptable derivative of a compound of formula (I) is formed, converting the said derivative into the parent compound of formula (I) or into an alternative pharmaceutically acceptable derivative of the compound of formula (I).

With regard to process A), the 5'-position in formula (II) may be protected with conventional protecting groups such as acyl groups, e.g. alkanoyl, substituted alkanoyl (for example alkoxyalkanoyl) or aroyl groups such as acetyl, methoxyacetyl or benzoyl; or ether groups for example, trialkylsilyl groups such as tert-butyldimethylsilyl; or other groups such as trityl or benzyl.

The protecting groups can subsequently be removed by acid or base hydrolysis, acyl groups being advantageously removed by base hydrolysis and silyl groups by acid hydrolysis or fluoride ion.

In process A), the starting compound of formula (II) may conveniently be prepared by reaction of a compound of formula (III)

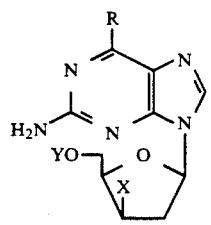

herein Y and R are as hereinbefore defined and X is a leaving group, such as an organosulfonate ester (e.g. methanesulfonate or trifluoromethanesulfonate) group conveniently by treatment with a suitable azide, for example, an alkali metal azide (e.g. lithium azide), in a polar aprotic solvent, for example, dimethylformamide (DMF) or dimethylsulfoxide (DMSO) at elevated temperature, for example 70° to 100° C.

Compounds of formula (III) may conveniently be prepared by 2'-deoxygenation of compounds of formula (IV)

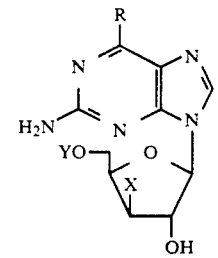

(wherein X, R and Y are as defined above), for example, by reaction with a trifluorotoluyl halide, such as, m-trifluorotoluyl chloride in the presence of a base, for example triethylamine or 4-dimethylaminopyridine (DMAP) in an inert solvent, for example, dichloromethane (DCM) followed by photolytic removal of the trifluorotoluyloxy group of the resulting trifluorotoluate, preferably in the presence of a photosensitizing agent, such as, 9-methylcarbazole to give the desired compound of formula (III).

Alternatively, compounds of formula (III) may conveniently be prepared by deoxygenation of compounds of formula (IV), for example typically by reaction with a thiocarbonate, such as o-phenylchlorothionoformate in the presence of a base, for example, DMAP in an inert solvent, for example, DCM to give the corresponding thiobenzoate followed by removal of the thiobenzoate by reduction using, for example, tri-n-butyltin hydride in the presence of azoisobutyronitrile at elevated temperatures.

Compounds of formula (IV) may be conveniently prepared by treatment of a compound of formula (V)

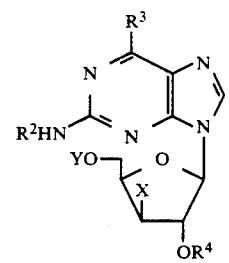

wherein X and Y are as defined above, $R^3$ is $OR^{3a}$, $NHR^{3b}$, halogen, amino which has two substituents selected from $C_{1-6}$ alkyl aryl, aralkyl including aracycloalkyl and $C_{3-6}$ cycloalkyl; or a 4- to 6-membered heterocyclic ring containing at least one nitrogen atom which ring is bonded to the purine base via the nitrogen atom, $R^2$ and $R^{3b}$ are amine protecting groups for example, acyl preferably acetyl, $R^{3a}$ is a hydroxy protecting group such as a carbamoyl group (e.g. diphenylcarbamoyl) and $R^4$ is a hydroxy protecting group, for example $C_{1-4}$ alkanoyl (e.g. acetyl) or aroyl (e.g. benzoyl) typically by treatment with acid, for example, hydrochloric acid to give the desired compound of formula (IV), said treatment being effected in the presence of an appropriate alkylating agent or amine for the preparation of a compound of formula (IV) wherein R is $C_{1-6}$ alkoxy; $C_{3-6}$ cycloalkyloxy; aryloxy or arylalkoxy; or a monosubstituted amino group (as defined above).

Compounds of formula (V) may be conveniently be prepared by reacting a compound of formula (VI)

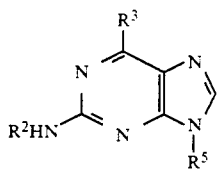

(VI)

(wherein $R^2$ and $R^3$ are as defined herein and $R^5$ is a leaving group, such as trimethylsilyl) with a sugar of formula (VII)

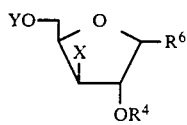

(VII)

(wherein Y, $R^4$ and X are as defined herein, $R^6$ is a leaving group, such as an ester (e.g. acetate or benzoate) or a halide group) in an inert solvent, such as toluene, in the presence of a Lewis acid, such as trimethylsilyl trifluoromethanesulfonate or stannic chloride.

Compounds of formula (VI) wherein $R^3$ is $OR^{3a}$ may conveniently be prepared by reacting the corresponding guanine derivative, prepared for example, according to the method of Zou and Robins, Can. J. Chem., 65(6) 1436-7 (1987) from guanine by reaction with an appropriate acylating agent, e.g. acetic anhydride to form a 2N,g-diacylguanine compound which is then treated with, for example, diphenylcarbamyl chloride. After removal of the N-9 acetyl group, a 2N-acyl-6-O-diphenylcarbamoyl guanine compound is formed, and subsequent reaction of this product with a silylating agent, such as N-O-bis (trimethylsilyl)acetamide in an inert solvent gives the desired compound of formula (VI). Other compounds of formula (VI) may be prepared in conventional manner for example in accordance with the method of Zou and Robins.

The compound of formula (VII) wherein the 1-substituent is a leaving group $R^6$ (as defined above) and the 2-substituent is a hydroxy protecting group $R^4$ (as defined above) may conveniently be prepared from the corresponding 3-X, 5-OY (X and Y as defined herein) 1.2-cyclic ketal by, for example, treatment with acetic anhydride/acetic acid and sulphuric acid when it is desired that $R^6$ and $R^4$ are acetyl.

The 3-X, 5-OY 1,2-cyclic ketal may be prepared from the corresponding 3-OH, 5-OY 1,2-cyclic ketal compound by, for example, in the case where X is mesyl, treatment with methanesulfonyl chloride and an organic base (e.g. triethylamine).

The 3-OH, 5-OY compound may be prepared from 1,2-O-isopropylidene-D-xylofuranose (Aldrich) by, for example, in the case where Y is methoxycarbonyl treatment with methyl chloroformate and an organic base (e.g. pyridine). The 1,2-O-isopropylidine-α-D-xylofuranose may also be prepared from D-xylose as described in U.S. Pat. No. 4,916,218.

For preparation of the compound of formula (I) wherein R is chlorine, compounds of formula (1) wherein R is $C_{1-3}$ alkoxy may be enzymatically converted to 3'-azido-2',3'-dideoxyguanosine (AZG) by treatment with commercially available adenosine deaminase. After protection of AZG's 5'-hydroxyl group, for example by acetylation, followed by chlorination with, for example, $POCl_3$, the 5'-acetyl protecting group may be removed by conventional means, in accordance with process (A).

With regard to process (B), the protecting groups $R_2$ and Y of compounds of formula (IIC) may be conventional amino and hydroxy protecting groups such as acyl groups, for example, alkanoyl such as acetyl or isobutyryl, or aroyl groups such as benzoyl; aralkyl groups, for example, a benzyl group; or trialkylsilyl groups such as tert-butyldimethylsilyl, the particular type of protecting group employed being dependant on the nature of the group to be protected. The protecting groups can be subsequently removed by conventional methods, for example, by acid or base hydrolysis. Acyl groups are typically removed by base hydrolysis and silyl groups by acid hydrolysis or fluoride ions.

Compounds of formula (IIA), wherein $R_2$ is as hereinbefore defined, either in the form of a salt such as an alkali metal for example, the N9- sodium salt, or in the form of a fully silylated derivative can be reacted with a compound of formula (IIB) wherein Y is as hereinbefore defined and A is a leaving group, for example, a halogen atom, such as chlorine, an acyloxy group such as acetoxy, an alkoxy group such as methoxy, in the presence of a catalyst such as tin (IV) chloride or trimethylsilyl triflate to a suitable solvent such as toluene.

Purine bases of formula (IIA) may be prepared from commercially available 2-amino-6-chloro purine (Sigma Chemical Co.). 2-Amino-6-O-substituted purines may be prepared from 2-amino-6-chloro purines by treatment with sodium and the appropriate alcohol. 2-Amino-6-N- substituted purines may be prepared by treatment of 2-amino-6-chloropurine with the appropriate amine or a compound of formula (VIII), in an organic solvent such as acetonitrile containing an organic base such as triethylamine. Followed by protection of the 2-amino group using methods known in the art to give the desired compound of formula (IIA).

Compounds of formula (IIB) may be prepared by methods well known to a skilled person or readily available in the chemical literature, for example, according to the method of G. W. J. Fleet and Jong Chan Son, (1987) Tetrahedron. Lett. Vol. 28 No. 31 pp 3615-3618.

Compounds of formula (I) may be prepared enzymatically in accordance with process C by reacting the purine base of formula (IID), wherein R is as hereinbefore defined, with a compound of formula (IIE) wherein B is as defined above, in the presence of a transferase enzyme, for example, N-deoxyribosyl transferase. The latter enzyme may be isolated by standard biochemical techniques from E. coli strain SS6030/14 which expresses lactobacillus enzyme, available from the American Type Culture Collection (ATCC), Rockville, Md. 20852-1776.

Compounds of formula (IIE), for example 3'-azido-3'-deoxythymidine, may be prepared by conventional methods including the method of Rideout et al U.S. Pat. No. 4,724,232 and 3'-azido-2',3'-dideoxy-guanosine may be prepared by the method of Imazawa and Eckstein, (1978), J.Org.Chem., Vol. 43, p3044-. The compounds of formula (IID) may be prepared from commercially available 2-amino-6-chloropurine (Sigma Chemical Co., St. Louis, Mo. 63178) 2-amino-6O-substituted purines may be prepared by treatment with sodium and the appropriate alcohol. 2-Amino-6-N-substituted purines may be prepared by treatment of 2-amino-6-chloropurine with the appropriate amine or a compound of formula (VIII) in an organic solvent, such as acetonitrile, containing an organic base, such as triethylamine.

In accordance with process (D), the compound of formula (I) wherein R is chlorine may be used for the preparation of compounds of formula (I) wherein R is $C_{1-6}$ alkoxy; $C_{3-6}$ cycloalkoxy, aryloxy; arylalkoxy in which the aryl may optionally be substituted with $C_{1-6}$ alkyl, $C_{1-6}$ alkoxy, halogen, nitro or hydroxyl; amino which is substituted by one or two substituents independently selected from $C_{1-6}$ alkyl, aryl, aralkyl and $C_{3-6}$ cycloalkyl; or a 4- to 6- membered heterocyclic ring containing at least one nitrogen atom which ring is bonded to the purine base via the nitrogen atom by methods known in the art for example in the case of 6-O-substituted purines by treatment with sodium and the appropriate alcohol, and, in the case of 6-N-substituted purines by treatment with the appropriate amine or a compound of formula (VIII)

(VIII)

(wherein n is 3–5) in the presence of an organic solvent such as acetonitrile or an alcohol such as methanol.

A compound of formula (1) may be converted into a pharmaceutically acceptable ester by reaction with an appropriate esterifying agent, e.g. an acid halide or anhydride. The compounds of formula (I), including esters thereof, may be converted into pharmaceutically acceptable salts thereof in a conventional manner, e.g. by treatment with an appropriate base. An ester or salt of a compound of formula (I) may be converted into the parent compound, e.g. by hydrolysis.

The present invention further includes the following novel intermediates which can be used in the processes outlined above.

1) 2-Amino-9-(3-azido-2,3-dideoxy-5-O-(methoxycarbonyl)-β-D-erythro-pentofuranosyl)-6-methoxy-gH-purine.
2) 2-Amino-9-(2-deoxy-3-O-mesyl-5-O-(methoxycarbonyl)-β-D-threopentofuranosyl)-6-methoxy-9H-purine.
3) 2-Amino-9-(3-O-mesyl-5-O-(methoxycarbonyl)-β-D-xylofuranosyl)-6-methoxy-9H-purine.
4) 2-Amino-9-(3-O-mesyl-5-O-(methoxycarbonyl)-2-O[(3-trifluoromethyl)benzoyl]-β-D-xylofuranosyl)-6-methoxy-9H-purine.
5) 2-Amino-9-(3-O-mesyl-5-O-(methoxycarbonyl)-2-O-(phenoxythiocarbonyl)-β-D-xylofuranosyl)-6-methoxy-9H-purine.
6) 2-Acetamido-9-(2-O-acetyl-3-O-mesyl-5-O-(methoxycarbonyl)β-D-xylofuranosyl)-6-[(diphenylcarbamoyl)oxy]-9H-purine.
7) 2-Amino-9-(3-azido-2,3-dideoxy-β-D-erythro-pentofuranosyl)-6-chloropurine.
8) 9-(5-O-Acetyl-3-azido-2,3-dideoxy-β-D-erythropentofuranosyl)-guanine.
9) 9-(5-O-Acetyl-3-azido-2,3-dideoxy-β-D-erythropentofuranosyl)-2-amino-6-chloro-9H-purine.

The following Examples illustrate the present invention but should not be constructed as a limitation thereof.

EXAMPLE I a) 5-Carbomethoxy-1,2-O-isopropylidene-β-D-xylofuranose

A solution of 1,2-O-ispropylidene-β-D-xylofuranose (Aldrich, 30.0 g, 0.1578 mol), dry pyridine (130 mL), and dry chloroform (60 mL) was cooled under nitrogen to 0° C. and methyl chloroformate (20.1 mL. 0.26 mol) was added dropwise over a 45-minute period such that the temperature did not exceed +10° C. The reaction was stoppered under nitrogen and placed in a cold room for 42.5 hours. After this time the reaction was brought to room temperature and diluted with $H_2O$ (630 mL). The reaction was shaken and the organic layer removed. The aqueous layer was extracted with chloroform (4×100 mL). The organic fractions were combined and dried over magnesium sulphate ($MgSO_4$). The $MgSO_4$ was filtered off and the filtrate concentrated in vacuo. The crude product was dried in vacuo for 2.5 h. The product was recrystallized from toluene:-hexane 1:1 (v/v).
69% yield mp 132°–133.5° C.
135.5°–136.5° C. (lit).

b) 1,2-O-Isopropylidene-3-O-mesyl-5-O-methoxycarbonyl-β-D-xylofuranose

The product of Stage a) (29.51 g, 0.119 mol), dry dichloromethane (DCM) (215 mL) and dry triethylamine (20.7 mL) was cooled to 0° C. under $N_2$ and methanesulfonyl chloride (1.25 eq., 11.5 mL) was added dropwise so that the temperature did not exceed 25° C. The reaction mixture was stirred at room temperature for 1.5 hours. The reaction was then stirred in a cold room overnight. After this time the reaction was quenched with brine (100 mL) and diluted with DCM (100 mL). The organic layer was set aside. The aqueous layer was back extracted with DCM (100 mL). The organic layers were combined, dried over $MgSO_4$, filtered, and concentrated. The product was purified on a flash chromatography silica gel column which was eluted with hexane:ethyl acetate (EtOAc) 2:1 (v/v). The appropriate fractions were combined, concentrated and stripped with DCM (2×100 mL). The product was dried overnight in vacuo to give the title compound 98% yield mp 56°–61° C.
Elemental Analysis: Calcd.: C, 40.46; H, 5.6; S, 9.80 Found: C, 40.57; H, 5.62; S, 9.87.

c) 1,2-Di-O-acetyl-3-O-mesyl-5-O-methoxycarbonyl-D-xylofuranose

The product of Stage b) (37.92 g, 0.116 mol) was dissolved in $Ac_2O$ (66 mL). cooled in an ice bath and acetic acid (480 mL) added. Concentrated $H_2SO_4$ (26.66 mL) was added over a 30 minute period and the solution was stirred overnight at room temperature. The solution was poured onto 900 mL of ice and water and the aqueous layer extracted with chloroform (4×850 mL). The organic layers were combined and extracted with 10% aqueous sodium hydrogen carbonate ($NaHCO_3$) (3×300 mL), dried over $MgSO_4$, filtered and concentrated. The product was purified on a flash chromatography column of silica gel, which was eluted with hexane:EtOAc 2:1 (v/v). The appropriate fractions were combined and concentrated to give the title compound 76% yield (oil).

d) 2-N,9-Diacetylquanine the product was synthesized according to the procedure of Zou and Robins, Can. J. Chem., 65(6), 1436-7 (1987). A solution of guanine (Aldrich, 60.44 g. 0.4 mol) dimethylacetamide (480 mL) and acetic anhydride (100 mL) was heated under nitrogen in a 160° C. oil bath overnight. The solution was cooled to room temperature and placed in a cold room for 6 days. The product which precipitated out of solution was filtered, the flask washed with hexane (3×50 mL). The product was rinsed with hexane (3×200 mL) and dried in vacuo overnight to give the title compound (111% yield).

e) 2-N-Acetyl-6-O-diphenylcarbamoylguanine (2-acetamido-6-diphenylcarbamoyloxypurine)

The product of Stage d) (5.88 g, 25 mmol) and dry pyridine (120 mL). diphenylcarbamyl chloride (6.37 g, 27.5 mmol) and dry diisopropylethylamine (8.7 mL) were stirred under nitrogen for 1.5 hours at room temperature. The solution was diluted with $H_2O$ (10 mL) and stirring continued for 10 minutes. The solution was concentrated in vacuo and stripped with toluene (3×20 mL). To the crude reaction was added 50% ethanol (EtOH): $H_2O$ (v:v) (300 mL) and the mixture was heated on a steam bath for 1.5 hours. The mixture was cooled to room temperature and placed in a cold room overnight. The product was filtered, washed with cold ethanol and dried in vacuo overnight to give the title compound (73% yield). This process was according to the method of Zou and Robins (1987). The NMR spectra agreed with the NMR reported in the literature.

f) 2-Acetamido-9-(2-O-acetyl-3-O-mesyl-5-0-methoxycarbonyl-$\beta$-D-xylofuranosyl)-6-((diphenylcarbamoyl)oxy)-9H-purine The general coupling procedure of Zou and Robins (1987) was used. A mixture of 2-N-acetyl-6-O-diphenylcarbamoylguanine (Stage e) 7.44 g, 17.71 mmol), dry 1 2-dichloroethane (192 mL), and N,O-bis(trimethylsilyl-)acetamide (9.60 mL) was heated at 80° C. under $N_2$ until a clear purple solution was generated. The 1,2-dichloroethane was removed by distillation under $N_2$. The mixture was cooled to room temperature and diluted with dry toluene (92 mL). Trimethylsilyltrifluoromethane sulfonate (4.80 mL) and the furanose derivative (Stage c) 9.11 g, 24.41 mmol in dry toluene (92 mL) were added. The reaction was heated under $N_2$ at 80° C. for 2 hours and then stirred at room temperature overnight. The reaction was cooled in an ice bath and diluted with saturated $NaHCO_3$ (12.9 mL). The layers were separated. The aqueous layer was extracted with EtOAc (3×20 mL). The organic fractions were combined, dried over $MgSO_4$. filtered and concentrated. The product was purified on a Prep 500 silica gel column to give the title compound 6.07 g (49% yield) as a light yellow foam.

g) 2-Amino-9-(3-O-mesyl-5-O-(methoxycarbonyl)-$\beta$-D-xylofuranosyl)-6-methoxy-9H-purine The product of Stage f) (5.96 g, 8.54 mmol) was mixed with 90 mL of methanolic hydrogen chloride, prepared by adding acetyl chloride (4 mL) dropwise to methanol (125 mL). The mixture was stirred under nitrogen at room temperature for 18 hours. The reaction was neutralized with solid $NaHCO_3$, filtered and concentrated. The product was purified on a flash chromatography column (silica gel) which was eluted with $CHCl_3$:MeOH 98:2 (v/v), 97:3 (v/v) and finally by 96:4 (v/v) to give the title compound (80% yield) as an off white foam.

h) 2-Amino-9-(3-O-mesyl-5-O-(methoxycarbonyl)-2-O-(phenoxythiocarbonyl)-$\beta$-D-xylofuranosyl)-6-methoxy-9H-purine The product of Stage g) (2.98 g, 6.865 mmol), dry $CH_3CN$ (51.5 mL), dry DCM (51.5 mL), DMAP (1.72 g, 14.04 mmol), and O-phenylchlorothionoformate (1.42 g, 8.238 mmol) were stirred at room temperature for 15 minutes and then diluted with saturated $NaHCO_3$ (10 mL). The mixture was stirred for 10 minutes and the layers separated. The aqueous layer was extracted with DCM (3×20 mL). The organic fractions were combined, dried over potassium carbonate ($K_2CO_3$), filtered and concentrated. The product was purified on a silica gel flash chromatography column which was eluted with chloroform followed by 98:2 (v/v) $CHCl_3$:MeOH to give the title compound 1.57 g (40% yield).

i) 2-Amino-9-(2-deoxy-3-O-mesyl-5-O-(methoxycarbonyl-$\beta$-D-threopentofuranosyl)-6-methoxy-9H-purine The product of Stage h) (1.57 g, 2.75 mmol) was dissolved in dry toluene (29 mL) and the solution purged with nitrogen for 10 minutes. Azoisobutyronitrile (AIBN) (96.5 mg, 0.59 mmol) and tri-n-butyltin hydride (0.97 mL) were added and the reaction heated at 80° C. for 40 minutes. The reaction was then cooled and concentrated.

The crude material was dissolved in $CH_3CN$ (50 mL) and the layer extracted with hexane (4×30 mL). The product was purified on a silica gel flash chromatography column eluted with 98:2 (v/v) $CHCl_3$:MeOH to give the title compound (39% yield) as a white foam.

An alternative process for the conversion of the 2-amino-9-(3-$\beta$-mesyl-5-O-(methoxycarbonyl)-$\beta$-D-xylofuranosyl)-6-methoxy-9H-purine to 2-amino-9-(2'-deoxy-3'-O-mesyl-5'-O-(methoxycarbon-yl)-$\beta$-D-threopentofuranosyl)-6-methoxy-9H-purine involves Stages h') and i') which are as follows:

h') 2-Amino-9-(3-O-mesyl-5-O-(methoxycarbonyl-2-0-(3-trifluormeth-yl)benzoyl-$\beta$-D-xylofuranosyl)-6-methoxy-9H-purine The product of Stage g (2.2 g, 5 mmol) dissolved in 20 mL of anhydrous methylene chloride was placed in a flask under nitrogen. The mixture was cooled in an ice bath and 1.06 mL (7.6 mmol) of freshly distilled triethylamine was added. 3-(Trifluoromethyl)benzoyl chloride (1.15 mL, 7.6 mmol) was then added dropwise to the reaction. When the addition was complete, 279 mg (2.28 mmol) of 4-dimethylaminopyridine was added. The reaction was stirred for 30 minutes in an ice bath, then for 2 hours at room temperature. The reaction mixture was diluted with 20 mL of DCM extracted with 10 mL of a saturated sodium bicarbonate solution and then 10 mL of brine. The organic layer was dried with $MgSO_4$, filtered and concentrated. The sample was chromatographed on silica gel eluting with 2% MeOH/$CHCl_3$ to give 2.1 g of the title compound as a yellow foam.

$^1$H NMR (200 MHz DMSO-$d_6$): 3.72 ($OCOCH_3$, 3H); 3.99 (6-$OCH_3$, 3H); 6.48 ($NH_2$, 2H).

i')
2-Amino-9-(2-deoxy-3-O-mesyl-5-O-(methoxycarbonyl)-β-D-threo-pentofuranosyl)-6-methoxy-9H-purine In a photoreaction vessel the product of Stage h' (900 mg, 1.5 mmol) and 9-methylcarbazole (489 mg, 2.6 mmol) were dissolved in 550 mL of i-propanol - water (v/v, 10:1). The reaction vessel was purged with $N_2$ for 15 minutes before irradiation for 4.4 hours. The sample was concentrated in vacuo. A second reaction was run using 1.2 g (1.98 mmol) of the product of Example h' and 652 mg (3.6 mmol) of 9-methylcarbazole. The reaction was irradiated for 3.8 hours. The two reactions were combined and adsorbed onto 12 g of silica gel and flash chromatographed on silica gel eluting with 1% MeOH/CHCl$_3$ then 2% MeOH/CHCl$_3$ to give 430 mg of the title compound as a yellow foam. NMR analysis supported the product structure.

$^1$H NMR (200 MHz, DMSO-d$_6$): 3.95 (6-OCH$_3$, 3H); 3.69 (OCOCH$_3$, 3H); 6.20 (H$_1$, 1H, dd); 6.49 (NH$_2$, 2H); 7.89 (H8, 1H).

J)
2-Amino-9-(3-azido-2,3-dideoxy-5-O-(methoxycarbonyl)-β-D-erythro-pentofuranosyl)-6-methoxy-9H-purine The product of Stage i) (174 mg) was dissolved in dry dimethylformamide (DMF) (3.3 mL) and lithium azide (LiN$_3$) (51.95 mg, 1.066 mmol) added. The reaction was heated at 80°-85° C. for 1 hour 35 minutes and then at 100° C. for 50 minutes. The reaction was concentrated and the product purified on a silica gel flash chromatography column, which was eluted with chloroform followed by 98:2 (v/v) CHCl$_3$:MeOH to give the title compound (74% yield) as a clear glass like oil.

k)
2-Amino-9-(3-azido-2,3-dideoxy-β-D-erythro-pentofuranosyl)-6-methoxy-9H-purine The product from Stage j) (92.5 mg, 0.254 mmol) was dissolved in MeOH (1.9 mL) and a solution containing MeOH (1.7 mL) and NaOMe (16.6 mg, 0.304 mmol) added. The solution was stirred at room temperature for 1 hour and then neutralized with 1N HCl and concentrated. The product was purified on a silica gel flash chromatography column which was eluted with CHCl$_3$ followed by 98:2 (v/v) CHCl$_3$:MeOH to give the title compound, yield 59.4 mg. A 43.9 mg sample was dissolved in 0.6 mL 50:50 (v/v) H$_2$O:MeOH and purified on an IBM C-18 1 cm×25 cm column (HPLC prep column). The column was eluted with 50:50 MeOH:H$_2$O (v/v) to give the title compound, yield 37.5 mg 99.7% pure by HPLC analysis.

High resolution EI mass spectrum: Calculated C$_{11}$H$_{14}$N$_8$O$_3$ 306.1189 Found C$_{11}$H$_{14}$N$_8$O$_3$ 306.1181

EXAMPLE 2 a) 2-Amino-6-methoxypurine

Sodium (4.7 g, 206.5 mmol, Aldrich lot #9621Cl) was added in portions to anhydrous methanol (125 mL). Upon complete dissolution, 2-amino-6-chloropurine (7.0 g, 41.3 mmol; Sigma lot #69F4064) was added and the reaction stirred at ambient temperature for 72 hours. The reaction was neutralized with Dowex 50W×12 (H+ form) (BioRad, 140-270 mesh) an acidic ion exchange resin. The resin was filtered and the filtrate reduced in volume to give a precipitate. The solid product was collected giving 4.2 g (23.9 mmol; 57.8%); mp >250° C.

UV: pH 1 λmax=285 (ε=11200), λmin=252 (ε=1900), pH 13 λmax=282 (ε=8100), λmin=257 (ε=3500), λsh=244 (ε=4500).

$^1$H NMR (DMSO-d$_6$) δ 7.9 (s, 1H, H8), 6.4 (br s, 2H, NH$_2$), 3.9 (s, 3H, CH$_3$).

Calcd. for C$_6$H$_7$N$_5$O and 0.3 HCl: C, 40.93; H, 4.18; N, 39.77; Cl, 6.04; Found: C, 41.08; H, 4.10; N, 39.84; Cl, 5.75.

b) Preparation of trans-N-deoxyribosylase from *Esherichia coli*

*E. coli* strain SS6030/14 was grown overnight (15-20 hr) in a rich medium, such as Luria broth, containing 150 g/ml ampicillin. The bacteria were collected from the growth medium by centrifugation at 4° C. and the cell pellet washed with cold, 100 mM sodium phosphate buffer, pH 6.0. A cell extract was prepared by resuspending the washed cell pellet with 0.6-0.8 volumes of cold, 100 mM sodium phosphate buffer followed by passage of the cell suspension through a French press at 12-14 Kpsi. Whole cells and cell debris were removed by centifugation in a 70Ti rotor at 50 Krpm for 90 min. The supernatant obtained following centrifugation was the high speed supernatant (HSS). The A$_{260}$ for the HSS was adjusted to equal 180 by addition of cold, 100 mM sodium phosphate buffer. The diluted HSS was adjusted to 0.2% PEI (polyethyleneimine), incubated at 4° C. for 15-30 min and then centrifuged. The supernatant obtained following the PEI precipitation was adjusted to 30% saturation with respect to incubated at 4° C. for 60-90 min and then centrifuged to pellet the protein. The protein precipitated with 30% (NH$_4$)$_2$SO$_4$ was slowly dissolved in 100 mM sodium phosphate buffer (pH 6.0) and then dialyzed against 2 to 6 liters of the same buffer.

After dialysis, the precipitate that formed was removed by centrifugation. The supernatant containing enzyme was heated 5-10 min in a 60° C. water bath followed by a 20 min incubation in a ice/water slurry. The precipitate that formed during the heat treatment step was removed by centrifugation. The supernatant contained trans-N-deoxyribosylase which was used for nucleoside synthesis.

The trans-N-deoxyribosylase activity of each enzyme preparation was quantitated using deoxyinosine and cytosine as substrates in the xanthine oxidase coupled assay system described by Cardinaud, R. 1978. Nucleoside Deoxyribosyltransferase from *Lactobacillus helveticus*. Methods Enzymol. 51:446-455.

*E. coli* strain SS6030/14 was deposited at the American Type Culture Collection, (ATCC) Rockville, Md 20852-1776 on Jul. 18, 1990 under Accession No. ATCC 68367.

c) 2-Amino-9-(3-azido-2,3-dideoxy-β-D-erythro-pentofuranosyl)-6-methoxy-9H-purine To 700 mL of an aqueous pH 6.0, 50 mM citrate buffer, prepared by addition of 8.41 g of citric acid to 800 mL of distilled deionized water and adjusting the final pH to 6.0 with sodium hydroxide, was added 2-amino-6-methoxypurine (0.116 g, 0.7 mmol) and 3'-azido-3'-deoxythymidine (0.935 g, 3.5 mmol). Solution was achieved by heating the mixture at 50° C. with sonication. A sample was removed as a control. A 25 mL solution of trans-N-deoxyribosylase at an activity of 429 units/mL was added. The reaction was heated at 50° C. Four days later, another 25 mL of enzyme was added. Nine days after the reaction was started, 0.109 g, 0.66 mmol of 2-amino-6-methoxypurine dissolved in 5 mL of citrate buffer was added to the reaction. The reaction was terminated after twenty-one days. The reaction was heated to 80° C. to precipitate the enzyme. The mixture was centrifuged and the supernatant, containing the product was collected. Most of the water was removed in vacuo. The aqueous solution was extracted with ethyl acetate (three times) to remove the product. The combined ethyl acetate fractions were dried with magnesium sulfate, filtered and the solvent removed in vacuo to give a foam. The foam was chromatographed on 180 g of silica gel (230–400 mesh) eluted with chloroform/methanol (99:1, v/v). The product containing fractions were combined and the solvent removed in vacuo to give the product as a foam (41% yield).

| UV: pH 1 | $\lambda max = 287$ ($\epsilon = 10300$), $\lambda min = 260$ ($\epsilon = 4100$) |
|---|---|
| | $\lambda max = 243$ ($\epsilon = 7800$), $\lambda min = 230$ ($\epsilon = 6400$) |
| pH 13 | $\lambda max = 279$ ($\epsilon = 9400$), $\lambda min = 260$ ($\epsilon = 5300$) |
| | $\lambda max = 247$ ($\epsilon = 9600$), $\lambda min = 225$ ($\epsilon = 4400$) |

$^1$H NMR (DMSO-$d_6$) $\delta$ 8.08 (s, 1H, 8H). 6.49 (s, 2H, 2NH$_2$), 6.14 (t, J=6.5 Hz, 1H, 1'H), 5.13 (t, J=5.5 Hz, 1H, 5'OH), 4.60–4.57 (m, 1H, 3'H), 3.93 (s, 1H, 6-OH$_3$), 3.90–3.83 (m, 1H, 4'H), 3.58–3.47 (m, 2H, 5'H), 2.86–2.76 and 2.46–2.39 (m, 2H, 2'H).

Calcd. for $C_{11}H_{14}N_8O_3$ with 0.1 CHCl$_3$ and 0.3 H$_2$O: C, 41.20; H, 4.68; N, 34.62; Found: C, 41.02; H, 4.40; N, 34.65.

EXAMPLE 3 a) 3'-Azido-2',3'-dideoxyguanosine

2-Amino-9-(3'-azido-2',3'-dideoxy-$\beta$-D-ribofuranosyl)-6-methoxy-9H-purine (Example 2c) (1.42 g, 4.64 mmol) was dissolved in 150 mL water. Adenosine deaminase (Boehringer-Mannheim lot #11416025-38, 10 mg/mL, 3.5 mL) was added and the reaction stirred at ambient temperature for 3.5 hours. The resulting suspension was filtered. The precipitate was washed with water then dried under high vacuum to yield 1.168 g (4 mmol, 86.2%); mp>250° C.

| UV: pH 1 | $\lambda max = 255$ ($\epsilon = 13000$), $\lambda min = 239$ ($\epsilon = 9100$), |
|---|---|
| pH 13 | $\lambda max = 265$ ($\epsilon = 12700$), $\lambda min = 240$ ($\epsilon = 8600$) |

$^1$H NMR (DMSO-$d_6$) $\delta$ 10.67 (sm 1H, NH), 7.92 (s, 1H, H8), 6.51 (br s, 2H, NH2), 6.05 (t, J=6.49 Hz, 1H, H1'), 5.11 (t, J=5.27 Hz, 1H, 5' OH), 4.59–4.51 (m, 1H, H3'), 3.89–3.82 (m, 1H, H4') 3.60–3.46 (m, 2H, H5'), 2.82–2.68 (m, 1H, H2'), 2.50–2.37 (m, 1H, H2').

Calcd. for $C_{10}H_{12}N_8O_3 \cdot 0.25 H_2O$: C, 40.47; H, 4.25; N, 37.76; Found: C, 40.50; H, 4.31; N, 37.65.

b) 9-(5-O-Acetyl-3-azido-2,3-dideoxy-$\beta$-D-erythro-pentofuranosyl)-quanine

In a 100 mL 3-neck round bottomed flask (oven dried) under N$_2$ was placed 633 mg 3'-azido-2',3'-dideoxyguanosine (2.2 mmol) in 10 mL anhydrous methylene chloride. To this was added triethylamine (0.34 mL. 2.4 mmol), 4-dimethylaminopyridine (27 mg, 0.22 mmol) and acetic anhydride (0.23 mL, 2.4 mmol).

The resulting mixture was stirred at room temperature for 4 h. TLC (20% MeOH/CHCl$_3$) showed no starting material remaining. The reaction was concentrated in vacuo and then flash chromatographed on silica gel eluted with 10% MeOH/CHCl$_3$ to give 347 mg (47% yield) of 9-(5'-O-acetyl-3'-azido-2',3'-dideoxy-$\beta$-D-erythro-pentofuranosyl) guanine.

Analytical data (EI)

MS M+ 334

NMR (200 mHz) DMSO-$d_6$ $\delta$ 10.68 (br s, NH) 7.8 (s, H8), 6.5 (br s, NH$_2$), 6.0 (dd), 2.0 (s, CH$_3$CO).

c) 9-(5-O-Acetyl-3-azido-2,3-dideoxy-$\beta$-D-erythro-pentofuranosyl) -2-amino-6-chloro-9H-purine In an oven dried 25 mL round bottomed flask outfitted with a condenser under N$_2$ was placed 50 mg 9-(5-O-acetyl-3-azido-2,3-dideoxy-$\beta$-D-erythro-pentofuranosyl)guanine in 70 $\mu$L N,N-diethylaniline (freshly distilled from CaH$_2$) and 0.2 mL POCl$_3$ (freshly distilled). The mixture was then immersed into an 115° C. oil bath for 3 min. The solution turned green, then yellow and finally orange in color. The excess POCl$_3$ was immediately removed under aspiration vacuum. The remaining residue was treated with ice and neutralized with NaHCO$_3$. The mixture was extracted with methylene chloride (2×10 mL) dried over MgSO$_4$, filtered and concentrated in vacuo. The resulting oil was chromatographed on basic alumina (CHCl$_3$) to yield 9-(5-O-acetyl-3-azido-2,3-dideoxy-$\beta$-D-erythro-pentofuranosyl)-2-amino-6-chloro-9H-purine in an 8% yield.

MS M+ 352 (EI)

NMR (300 mHz) CDCl$_3$ 7.8 (s, H8), 6.2 (dd), 5.2 (br s, NH$_2$), 1.57 (s, CH$_3$CO).

d) 2-Amino-9-(3-azido-2,3-dideoxy-$\beta$-D-erythro-pentofuranosyl)-6-chloro-9H-purine In a 10 mL round bottomed flask was placed 12 mg of 9-(5-O-acetyl-3-azido-2,3-dideoxy-$\beta$-D-erythro-pentofuranosyl)-2-amino-6-chloro-9H-purine in 2 mL freshly prepared solution of ammonia in methanol (methanolic-ammonia). The mixture was stirred 1 h at room temperature. TLC (90:10 CHCl$_3$/MeOH) showed the reaction was complete. The sample was concentrated in vacuo and then chromatographed on alumina eluted with CHCl$_3$/MeOH (98:2) to give a quantitative yield of 2-amino-9-(3'-azido-2',3'-dideoxy-$\beta$-D-erythro-pentofuranosyl)-6-chloro-9H-purine; mp=134°–136° C.

MS (M + 1)311 (EI)

NMR (300 mHz) CHCl$_3$ 7.81 (s, H8), 6.14 (dd, J=9.5, 5.8 Hz, H1'), 5.68 (d, J=10.7 Hz, OH), 5.18 (br s, NH$_2$), 4.58 (dt, J=6.3, 1.9, 1.9 Hz, H3'), 4.22 (app. q, J=2.0 Hz, H4'), 4.0 (d, J=12.8 Hz, H5B), 3.79 (dd, J=12.8, 10.7 Hz, H5A), 3.09 (ddd, J=13.7, 8.9, 6.4 H2$\alpha$), 2.33 (ddd, J=13.9, 5.6, 1.7 Hz, H2$\beta$).

$^1$H NMR DMSO-$d_6$ $\delta$ 8.36 (s, H8), 6.19 (t, J=6.3 Hz, H1'), 5.12 (t, J=5.2 Hz, OH). 7.00 (br s, NH2), 4.62 (dd, J=5.3 Hz, H3'), 3.90 (dd, J=4.8 Hz, H4'), 3.58 (AB, H5B), 2.88 (ddd, J=13.0, 5.9. 5.9 Hz, H2α), 2.49 (obscured partially by DMSO).

EXAMPLE 4

2-Amino-9-(3-azido-2,3-dideoxy-β-D-erythro-pentofuranosyl)-6-chloro-9H-purine To 500 mL of an aqueous pH 6.0, 50 mM citrate buffer, prepared as described in Example 2c, was added 2-amino-6-chloropurine (0.0848 g, 0.5 mmol, Sigma lot #69F4064) and 3'-azido-3'-deoxythymidine (0.668 g, 2.5 mmol). Solution was achieved by heating the mixture at 50° C. with sonication. A sample was removed as a control. A 24 mL solution of trans-N-deoxyribosylase (Example 2b) at an activity of 1400 units/mL was added. The reaction was heated at 50° C. Seven days later 0.0848 g, 0.5 mmol, of 2-amino-6-chloropurine was added to the reaction. The reaction was terminated after fourteen days. The reaction was heated to 80° C. to precipitate the enzyme and then filtered. The aqueous solution was extracted with ethyl acetate to remove the product. The combined ethyl acetate fractions were dried with magnesium sulfate filtered and the solvent removed in vacuo to give a foam. The foam was chromatographed on 90 g of silica gel (230–400 mesh) eluted with chloroform/methanol (96:4, v/v). The product containing fractions were combined and the solvent removed in vacuo to give the product as a solid. The solid was recrystallized from water to give the product as a 0.25 hydrate (46% yield). m.p.=113°–115° C.

| UV: pH 1 | λmax = 310 (ε = 8000), λmin = 266 (ε = 1300), |
| --- | --- |
| | λmax = 246 (ε = 7100), λmin = 235 (ε = 5900) |
| pH 13 | λmax = 306 (ε = 8800), λmin = 265 (ε = 2100), |
| | λmax = 246 (ε = 8200), λmin = 225 (ε = 6800) |

$^1$H NMR (DMSO-d$_6$) δ 8.34 (s, 1H, 8H). 6.98 (s, 2H, 2NH$_2$), 6.17 (t, J=6.3 Hz, 1H, 1'H), 5.09 (t, J=5.6 Hz, 1H, 5'OH), 4.64-4.56 (m, 1H, 3'H), 3.92-3.85 (m, 1H, 4'H), 3.65-3.47 (m, 2H, 5'H), 2.93-2.80 and 2.53-2.40 (m, 2, 2'H).

Calcd. for C$_{10}$H$_{11}$ClN$_8$O$_2$ and 0.25 H$_2$O: C, 38.11; H, 3.68; N, 35.55; Cl, 11.25; Found: C, 37.97; H, 3.67; N, 35.51; Cl, 11.28.

EXAMPLE 5 a) 2-Amino-6-propoxypurine

Sodium (0.68 g, 29.5 mmol Aldrich lot #9621CL) was added in portions to anhydrous propanol (25 mL). Upon complete dissolution 2-amino-6-chloropurine (1 g, 5.9 mmol, Sigma lot #69F4064) was added and the reaction heated in an 85° C. oil bath under a nitrogen atmosphere for 20 hours. The solution was cooled and neutralized with Dowex 50W×12 (H+ form) (BioRad, 140-270 mesh), an acidic ion exchange resin. The resin was filtered, the filtrate collected and adsorbed onto silica gel column and eluted with CHCl$_3$/MeOH (9:1, v/v). Combination and evaporation of appropriate fractions gave 0.89 g of slightly impure material. Adsorption of this material onto silica gel followed by elution with EtOAc/MeOH (10:1, v/v) gave, after evaporation of combined product fractions, 0.76 g, (3.9 mmol; 67%). mp=198°–200° C.

| UV: pH 1 | λmax = 285 (ε = 11900) λmin 252 (ε = 2000) |
| --- | --- |
| pH 13 | λmax = 283 (ε = 8400) λmin 257 (ε = 3500) |

$^1$H NMR (DMSO-d$_6$) δ 12.4 (br s, 1H, H9), 7.77 (s, 1H, H8), 6.19 (s, 2H, NH$_2$), 4.32 (t, J=6.8 Hz, 2H, OCH$_2$), 1.83-1.65 (m, 2H, CH$_2$), 0.95 (t, J=7.3 Hz, 3H, CH$_3$).

Calcd. for C$_8$H$_{11}$N$_5$O: C, 49.73; H, 5.74; N, 36.25; Found: C, 49.78; H, 5.78; N, 36.20.

b) 2-Amino-9-(3-azido-2,3-dideoxy-β-D-erythro-pentofuranosyl)-6-propoxy-9H purine To 500 ml of an aqueous pH 6.0 50 mM citrate buffer, prepared as described in Example 2c, was added 2-amino-6-propoxypurine (0.0985 g, 0.5 mmol) and 3'-azido-3'-deoxythymidine (0.668 g, 2.5 mmol). Solution was achieved by heating the mixture at 50° C. with sonication. A sample was removed as a control. A 25 mL solution of trans-N-deoxyribosylase (Example 2b) at an activity of 1500 units/mL was added. The reaction was heated at 50° C. Seven days later 0.0985 g, 0.5 mmol, of 2-amino-6-propoxypurine was added to the reaction. Eleven days after the reaction was started, another 0.0985 g, 0.5 mmol, of 2-amino-6-propoxypurine was added to the reaction. The reaction was terminated after twenty-three days. The reaction was heated to 80° C. to precipitate the enzyme and then filtered. The aqueous solution was extracted with ethyl acetate to remove the product. The combined ethyl acetate fractions were dried with magnesium sulfate, filtered, and the solvent was removed in vacuo to give a foam. The foam was chromatographed on 180 g of silica gel (230-400 mesh) eluted first with chloroform/methanol (99:1, v/v) then with chloroform/methanol (98:2, v/v). The product containing fractions were combined and the solvent removed in vacuo to give the product as an oil. The oil was dissolved in water and lyophilized to give a solid (56% yield). mp=145°–147° C.

| UV: pH 1 | λmax = 287 (ε = 9800) λmin = 260 (ε = 3400) |
| --- | --- |
| | λmax = 243 (ε = 7000) λmin = 232 (ε = 5800) |
| pH 13 (nm) | λmax = 280 (ε = 9900) λmin = 261 (ε = 5500) |
| | λmax = 247 (ε = 9900) λmin = 231 (ε = 6400) |

$^1$H NMR DMSO-d$_6$ δ 8.09 (s, 1H, 8H). 6.46 (s. 2H, 2NH2), 6.16 (t, J=6.2 Hz, 1H, 1'H), 5.15 (t, J=5.3 Hz, 1H, 5'OH), 4.63-4.58 (m, 1H, 3'H), 4.35 (t, J=6.7 Hz, 2H, 6—OCH$_2$), 3.91-3.87 (m, 1H, 4'H), 3.65-3.53 (m, 2H. 5'H). 2.89-2.80 and 2.51-2.40 (m, 2H, 2'H), 1.82-1.70 (m, 2H, —CH$_2$CH$_2$CH$_3$), 0.97 (t, J=7.3 Hz, 3H, —CH$_2$CH$_3$)

Calcd. for C$_{13}$H$_{18}$N$_8$O$_3$: C, 46.70; H, 5.43; N, 33.52; Found: C, 46.78; H, 5.47; N, 33.57.

EXAMPLE 6 a) 2-Amino-6-benzyloxypurine

Benzyl alcohol (6.4 g, 59 mmol Eastman lot #C4B) was diluted with anhydrous acetonitrile (5 mL) followed by addition of sodium (1.36 g, 59 mmol, Aldrich lot #9621CL) under nitrogen. After complete dissolution of the sodium, 2-amino-6-chloropurine (1 g, 5.9 mmol, Sigma lot #69F4064) was added and the reaction stirred at ambient temperature for 7 days. The reaction was filtered and the collected precipitate washed with cold acetonitrile. The solid was then dissolved in methanol and adsorbed onto silica gel (230-400 mesh). Elution with EtOAc/MeOH (9:1 v/v) followed by combination and evaporation of the appropriate fractions yielded 0.96 g (4 mmol; 67%); mp=203°–205° C.

UV: pH 1 λmax = 287 (ε = 12400) λmin = 253 (ε = 2200),
λmax = 284 (ε = 9100) λmin = 257 (ε = 3800)

$^1$H NMR (DMSO-d$_6$) δ 12.4 (br s, 1H, H9), 7.80 (s, 1H, H8), 7.51–7.28 (m, 5H, phenyl), 6.28 (br s, 2H, NH$_2$), 5.46 (s, 2H, OCH$_2$).

Calcd. for C$_{12}$H$_{11}$N$_5$O and 1.0 mole CH$_3$OH: C, 57.13; H, 5.53; N, 25.63; Found: C, 57.13; H, 5.54; N, 25.70.

b) 2-Amino-9-(3-azido-2,3-dideoxy-β-D-erythro-pentofuranosyl)-6-benzyloxy-9H-purine To 800 mL of an aqueous pH 6.0, 50 mM citrate buffer, prepared as described in Example 2c, was added 2-amino-6-benzyloxy-purine (0.193 g, 0.8 mmol) and 3'-azido-3'-deoxythymidine (1.069 g, 34.0 mmol). Solution was achieved by heating the mixture at 50° C. with sonication. A sample was removed as a control. A 40 mL solution of trans-N-deoxyribosylase (Example 2b) with an activity of 1500 units/mL was added. The reaction was heated at 50° C. Four days later, 0.193 g, 0.8 mmol, of 2-amino-6-benzyloxypurine was added to the reaction. A precipitate was noted. Twelve days after the reaction was started, another 0.193 g, 0.58 mmol, of 2-amino-6-benzyloxypurine and 0.428 g, 1.6 mmol, of 3'-azido-3'-deoxythymidine were added to the reaction. Nineteen days after the reaction was started, 0.193 g, 0.58 mmol, of 2-amino-6-benzyloxypurine was added to the reaction. The reaction was stopped after twenty-six days. The reaction was chilled to 0° C. for several hours then filtered. The cake was found to contain the product. The cake was extracted with hot ethanol then filtered. The solvent was removed in vacuo to give the crude product as a solid. The solid was chromatographed first on 150 g of silica gel (230–400 mesh) eluted with chloroform/methanol (98:2. v/v) then on basic alumina, 90 g, eluted with chloroform/methanol (98:2, v/v). The product containing fractions were combined and the solvent removed in vacuo to give the product as a foam (26% yield).

UV: pH 1 λmax = 289 (ε = 9810) λmin = 261 (ε = 3300),
λmax = 243 (ε = 7100)
pH 13 λmax = 281 (ε = 11200) λmin = 261 (ε = 5800),
λmax = 247 (ε = 10800)

$^1$H NMR (D 8.08 (s, 1H, 8H), 7.50–7.30 (m, 5H, Ph), 6.52 (s, 2H, 2NH2), 6.15 (t, J=6.3 Hz, 1H, 1'H), 5.48 (s, 2H, —OCH$_2$Ph), 5.11 (t, J=5.5 Hz, 1H, 5'OH), 4.63–4.54 (m, 1H, 3'H), 3.91–3.84 (m, 1H, 4'H), 3.58–3.45 (m, 2H, 5'H), 2.89–2.76 and 2.47–2.36 (m, 2H, 2'H).

Calcd. for C$_{17}$H$_{18}$N$_8$O$_3$ and 0.2 H$_2$O: C, 52.90; H, 4.80; N, 29.03; Found: C, 53.24; H, 4.88; N, 28.74.

EXAMPLE 7 a) 2-Amino-6-dimethylaminopurine

2-Amino-6-chloropurine (15 g, 88.4 mmol Sigma lot 9F4064) was dissolved in dimethylamine (195 mL, 25% in H$_2$O. Eastman lot b6B) and heated at reflux for 90 minutes. The reaction was cooled and the resulting precipitate filtered. The precipitate was recrystallized from 500 mL MeOH to give 11.2 g (63 mmol; 71%); mp=254°–256° C.

UV: pH 1 λmax 283, 255, 228 (ε = 13800, 12700, 11000).
λmin 267, 240, 216 (ε = 10400, 9400, 9500),
pH 13 λmax 291 (ε = 12500), λmin 261 (ε = 4000)

$^1$H NMR (DMSO-d6) 12.08 (s, 1H, NH), 7.62 (s, 1H, H8), 5.63–5.58 (m 2H, NH2), 3.34 (s, 6H, 2CH3).

Calcd. for C$_7$H$_{10}$N$_6$ and 0.3 H$_2$O: C, 45.79; H, 5.82; N, 45.77. Found: C, 45.83; H, 5.84; N, 45.75.

b) 2-Amino-9-(3-azido-2,3-dideoxy-β-D-erythro-pentofuranosyl)-6-dimethylamino-9H-purine To 500 mL of an aqueous pH 6.0, 50 mM citrate buffer, prepared as described in Example 2c, was added 2-amino-6-dimethylaminopurine (0.0891 g, 0.5 mmol) and 3'-azido-3'-deoxythymidine (0.668 g, 2.5 mmol). Solution was achieved by heating the mixture at 50° C. with sonication. A sample was removed as a control. A 24 mL solution of trans-N-deoxyribosylase (Example 2b) at an activity of 1400 units/mL was added. The reaction was heated at 50° C. Seven days later 0.0891 g, 0.5 mmol, of 2-amino-6-dimethylamino purine was added to the reaction. The reaction was terminated after fourteen days. The reaction was heated to 80° C. to precipitate the enzyme and then filtered. The aqueous solution was extracted with ethyl acetate to remove the product. The combined ethyl acetate fractions were dried with magnesium sulfate, filtered, and the solvent was removed in vacuo to give a foam. The foam was chromatographed on 90 g of silica gel eluted with chloroform/methanol (97:3, v/v). Chromatography a second time on silica gel (230–400 mesh) eluted with chloroform/methanol (98:2, v/v) gave pure product. The product containing fractions were combined and the solvents removed in vacuo to give the product as a solid (41% yield).

UV: pH 1 λmax = 293, (ε = 8900) λmin = 274 (ε = 6200),
λmax = 257, (ε = 9300) λmin = 240 (ε = 6000),
pH 13 (nm) λmax = 284 (ε = 12700),
λmin = 248 (ε = 6400)

$^1$H NMR (DMSO-d$_6$) δ 7.93 (s, 1H, 8H), 6.13 (t, J=6.5 Hz, 1H 1'H), 5.84 (br s, 2H, 2NH$_2$), 5.26 (t, J=5.6 Hz, 1H, 5'OH), 4.61–4.53 (m, 1H, 3'H), 3.91'3.84 (m, 1H, 4'H), 3.59–3.53 (m, 2H, 5'H), 3.33 (br s, 6H, N(CH$_3$)$_2$), 2.45–2.36 (m, 2H, 2'H).

Calcd. for C$_{12}$H$_{17}$N$_9$O$_2$: C, 45.14; H, 5.37; N, 39.48 Found: C, 44.91; H, 5.46; N, 39.28.

EXAMPLE 8

2-Amino-9-(3-azido-2,3-dideoxy-β-D-erythro-pentofuranosyl)-6- methyl-amino-9H-purine 2-Amino-9-(3'-azido-2',3'-dideoxy-β-D-erythro-pentofuranosyl)-6-chloropurine (0.35 g, 1.13 mmol) was refluxed in 88 mL methylamine (40% in water; Kodak lot #B17A) for 15 minutes. The reaction was cooled and the solvent evaporated to give a foam. The foam was dissolved in CHCl$_3$: MeOH (99:1 v/v) and applied to a basic alumina column (Grade 1; Type WB-2). Elution followed by evaporation of appropriate fractions yielded an amorphous solid. The solid was dissolved in water and lyophilized to give 0.211 g (0.69 mmol; 61.2%);

UV: pH 1 λmax = 290, 255 (ε = 12000, 12300),
λmin = 272, 235 (ε = 8600, 6200),
pH 13 λmax = 280 (ε = 14400), λmin = 241 (ε = 5900),
λsh = 264 (ε = 11200)

$^1$H NMR (DMSO-d$_6$) δ 7.88 (s, 1H, H6), 7.22 (s, 1H, NH), 6.14–6.07 (m, 1H, H1'), 5.81 (s, 2H, NH$_2$), 5.3–5.2 (m, 1H, 5'OH), 4.61–4.53 (m, 1H, H3'), 3.90–3.88 (m, 1H, H4'), 3.6–3.5 (m, 2H, H5'), 2.9–2.7 (m, 4H, H2' and CH$_3$), 2.46–2.31 (m, 1H, H2').

Calcd. for C$_{11}$H$_{15}$N$_9$O$_2$: C, 43.27; H, 4.95; N, 41.29 Found: C, 43.15; H, 4.99; N, 41.16.

EXAMPLE 9

2-Amino-9-(3-azido-2,3-dideoxy-β-D-erythro-pentofuranosyl)-6-cyclopropylamino-9H-purine A 105 mL stainless steel bomb was charged with 2-amino-9-(3'-azido-2',3'-dideoxy-β-D-erythro-pentofuranosyl)-6-chloropurine (0.35 g; 1.13 mmol) in 88 mL anhydrous MeOH and cyclopropylamine (0.78 g; 21.5 mmol; Aldrich lot #8119TK). The bomb was sealed and placed in a 75° C. oven for 24 hours. The solvent was evaporated and the residue adsorbed onto silica gel (230–400 mesh). Chromatography using EtOAc/MeOH (98:2 v/v) followed by combination and evaporation of appropriate fractions yielded a sticky foam. The foam was dissolved in water and lyophilized to give 0.25 g (0.76 mmol; 66.8%) of product as a 0.25 hydrate.

UV: pH 1 λmax = 295, 255 (ε = 14000, 11000),
λmin = 273, 236 (ε = 6600, 5800),
pH 13 λmax = 283 (ε = 14900, 10000),
λmin = 263, 244 (ε = 10000, 7200).

$^1$H NMR (DMSO-d$_6$) δ 7.89 (s, 1H, H6), 7.36 (d, J=4.34 Hz, 1H, NH), 6.1 (t, 1H, H1'), 5.85 (s, 2H, NH2), 5.29 (t, 1H, 5═OH), 4.65–4.50 (m, 1H, H3'), 3.90–3.82 (m, 1H, H4'), 3.68–3.50 (m, 2H, H5'), 2.99 (s, 1H, CH), 2.9–2.8 (m, 1H, H2'), 2.46–2.30 (m, 1H, H2'), 0.7–0.6 (m, 4H, (CH$_2$)$_2$).

Calcd. for C$_{13}$H$_{17}$N$_9$O$_2$ and 0.25 H$_2$O: C, 46.49; H, 5.25; N, 37.54 Found: C, 46.54; H 5.26; N, 37.47.

EXAMPLE 10 a) 2-Amino-6-ethoxypurine

Sodium (0.68 g, 29.5 mmol, Aldrich lot #9621CL) was added in portions to anhydrous ethanol (50 mL). Upon complete dissolution 2-amino-6-chloropurine (1 g, 5.9 mmol Sigma lot #69F4064) was added and the reaction heated at reflux for 96 hours. The reaction was cooled, diluted with 20 mL water, and neutralized with 1N HCl. The solvents were evaporated and the residue slurried in 100 mL water. The product was filtered off and air dried to give 0.95 g (5.3 mmol; 89.9%); mp=252–°253° C.

UV: pH 1 λmax = 285, (ε = 14100), λmin = 251 (ε = 2300),
λsh = 231 (ε = 7300),
pH 13 λmax = 283 (ε = 9600), λmin = 257 (ε = 4000),
λsh = 244 (ε = 5100)

$^1$H NMR (DMSO-d$_6$) δ 12.42 (br s, 1H, NH), 7.82 (s, 1H, H8), 6.20 (s, 2H, NH$_2$), 4.44 (q, J=7.01 Hz, 2H, CH$_2$), 1.36 (t J=7.01 Hz, 3H, CH$_3$).

Calcd. for C$_7$H$_9$N$_5$O): C, 46.92; H, 5.06; N, 39.09 Found: C, 47.00; H, 5.10; N, 39.04.

b)
2-Amino-9-(3-azido-2,3-dideoxy-β-D-erythro-pentofuranosyl)6-ethoxy-9H-purine

To 500 mL of an aqueous pH 6.0, 50 mM citrate buffer, prepared as described in Example 2c, was added 2-amino-6-ethoxypurine (0.0895 g, 0.5 mmol) and 3'-azido-3'-deoxythymidine (0.668 g, 2.5 mmol). Solution was achieved by heating the mixture at 50° C. with sonication. A sample was removed as a control. A 24 mL solution of trans-N-deoxyribosylase (Example 2b) at an activity of 1400 units/mL was added. The reaction was heated at 50° C. Four days later 0.089 g, 0.5 mmol, of 2-amino-6-ethoxypurine was added to the reaction. The reaction was terminated after eleven days. The reaction was heated to 80° C. to precipitate the enzyme and then filtered. The aqueous solution was extracted with ethyl acetate to remove the product. The combined ethyl acetate fractions were dried with magnesium sulfate, filtered and the solvent removed in vacuo to give a foam. The foam was chromatographed on 180 g of silica gel (230–400 mesh) eluted with chloroform/methanol (98:2. v/v). The product containing fractions were combined and the solvent removed in vacuo to give the product as an oil. The oil was dissolved in water and lyophilized to give a solid (55% yield).

UV: pH 1 λmax = 287, (ε = 9500), λmin = 260 (ε = 3200),
λmax = 243, (ε = 6700), λmin = 231, (ε = 5500),
pH 13 λmax = 280 (ε = 9400), λmin = 260 (ε = 5300)
λmax = 247 (ε = 9400), λmin = 227 (ε = 5000)

$^1$H NMR (DMSO-d$_6$) δ 8.09 (s, 1H, 8H), 6.45 (s, 2H, 2NH$_2$), 6.14 (t, J=6.5 Hz, 1H, 1'H), 4.63–4.54 (m, 1H, 3'H), 4.43 (q, J=7.0 Hz, 2H, 6-OCH2-), 3.91–3.83 (m, 1H, 4'H), 3.57–3.48 (m, 2H 5'H), 2.86–2.76 and 2.47–2.39 (m, 2H, 2'H), 1.34 (t, J=7.0 Hz, 3H, 6-OCH$_2$CH$_3$).

Calcd. for C$_{12}$H$_{16}$N$_8$O$_3$: C, 45.00; H, 5.03; N, 34.98 ,Found: C, 44.94; H, 5.06; N, 34.89.

EXAMPLE 11 a) 2-Amino-6-isopropoxy-9H-purine

Sodium (Aldrich, lot #9621CL, 4.1 g, 176.9 mmol) was reacted with 150 mL of isopropanol, 2-Amino-6-chloropurine (Sigma, lot #69F4064, 6.0 g, 35.4 mmol) was added and the reaction stirred at 50° C. for 24 hours. The solution was cooled and brought to pH 7 with 1N HCl. The solvents were evaporated to one-half volume. The precipitate was filtered, washed with water and dried to give 5.9 g (30.5 mmol, 87%); mp=204°–206° C.

UV: pH 1 λmax = 285, (ε = 11400), λmin = 251, (ε = 1600),
λsh = 232 (ε = 5600)
pH 13 λmax = 284 (ε = 7600), λmin = 258 (ε = 3100)
λsh = 245 ( = 4100)

$^1$H NMR (DMSO-d$_6$) δ 12.35 (s, 1H, NH), 7.77 (s, 1H, H8), 6.13 (s, 2H, NH$_2$), 5.52–5.39 (m, 1H, OCH), 1.32 (d, J=6.25 Hz, 6H, 2 CH$_3$).

Calcd. for C$_8$H$_{11}$N$_5$O·0.15HCl: C, 48.36; H, 5.66; N, 35.25 Found: C, 48.25; H, 5.45; N, 35.39.

b)
2-Amino-9-(3-azido-2,3-dideoxy-β-D-erythro-pentofuranosyl)-6-isopropoxy-9H-purine To 800 mL of an aqueous pH 6.0, 50 mM citrate buffer, prepared as described in Example 2c. was added 2-amino-6-isopropoxypurine (0.159 g, 0.8 mmol) and 3'-azido-3'-deoxythymidine (1.069 g, 4.0 mmol). Solution was achieved by heating the mixture at 50° C. with sonication. A sample was removed as a control. A 40 mL solution of trans-N-deoxyribosylase (Example 2b) with an activity of 1500 units/mL was added. The reaction was heated at 50° C. Six days later, 0.159 g, 0.8 mmol, of 2-amino-6-isopropoxypurine was added to the reaction. Fifteen days after the reaction was started, another 0.159 g, 0.8 mmol, of 2-amino-6-isopropoxypurine and 0.428 g, 1.6 mmol, of 3'-azido-3'-deoxythymidine were added to the reaction. Twenty-seven days after the reaction was started, 0.159 g, 0.58 mmoles, of 2-amino-6-isopropoxypurine was added to the reaction. The reaction was stopped after thirty-three days. The reaction was heated at 80° C. to precipitate the enzyme and filtered. The aqueous solution was extracted with ethyl acetate to remove the product. The combined ethyl acetate fractions were dried with magnesium sulfate, filtered, and the solvent was removed in vacuo to give a foam. The foam was chromatographed on basic alumina grade 1 eluted with chloroform/methanol (95:5, v/v). The product containing fractions were combined and the solvent removed in vacuo to give the product as a foam (28% yield). mp=195°–197° C.

UV: pH 1 $\lambda max$ = 287, ($\epsilon$ = 17700), $\lambda min$ = 261, ($\epsilon$ = 6500),
$\lambda sh$ = 244 ($\epsilon$ = 12700)
pH 13 $\lambda max$ = 280 ($\epsilon$ = 17600), $\lambda min$ = 261 ($\epsilon$ = 10000)
$\lambda sh$ = 248 ($\epsilon$ = 17500)

$^1$H NMR (DMSO-$d_6$) δ 8.06 (s, 1H, 8H), 6.4 (br s, 2H, 2NH$_2$), 6.14 (t, J=6.44 Hz, 1H, 1'H), 5.5–5.4 (m, 1H, CH), 5.14 (t, J=5.6 Hz, 1H, 5OH), 4.6–4.5 (m 1H, 3'H), 3.9–3.8 (m, 1H, 4'H), 3.6–3.47 (m, 2H, 5'H), 2.89–2.76 and 2.5–2.4 (m, 2H, 2'H), 1.3 (d, J=6.25 Hz, 6H, (CH$_3$)$_2$).

Calcd. for C$_{13}$H$_{18}$8O$_3$: C, 46.70; H, 5.43; N, 33.52; Found: C, 46.97; H, 5.52; N, 33.28,

EXAMPLE 12

2-Amino-9-(3-azido-2,3-dideoxy-β-D-pentofuranosyl)-6-propylamino-9H-purine

2-Amino-9-(3'-azido-2', 3'-dideoxy-β-D-pentofuranosyl)-6-chloro-9H-purine (0.24 g, 0.87 mmol) was reacted with propylamine (Aldrich, 0.257 g, 4.36 mmol) in 10 mL anhydrous acetonitrile at 70° C. for 8 hours. The solvents were evaporated and the residue preloaded onto silica gel. Elution from a silica column with CHCl$_3$/MeOH (98:2, v/v) followed by combination and evaporation of appropriate fractions gave an oil. Coevaporation with EtOAc yielded the product as a foam, 0.22 g (0.66 mmol, 76%). mp=138°–140° C.

UV: pH 1 $\lambda max$ = 293, 255 ($\epsilon$ = 13000, 13100),
$\lambda min$ = 272, 237 ($\epsilon$ = 8900, 7600),
pH 13 $\lambda max$ = 281 ($\epsilon$ = 15200), $\lambda min$ 242 ($\epsilon$ = 6700),
$\lambda sh$ = 267 ($\epsilon$ = 11600)

$^1$H NMR (DMSO-$d_6$) δ 7.9 (s, 1H, 8H), 7.3 (s, 1H, NH), 6.1 (t, J=6.49 Hz, 1H, H1'), 5.8 (s, 2H, NH$_2$), 5.3 (t, J=6.04 Hz, 1H, 5'OH), 4.6-4.55 (m, 1H, H3'), 3.9-3.85 (m, 1H, H4'), 3.6-3.54 (m, 2H, H5'), 2.9-2.76 (m, 1H, H2'), 2.5-2.3 (m, 1H, H2'), 1.6-1.5 (m, 2H, CH$_2$), 0.8 (t, 3H, CH$_3$).

Calcd. for C$_{13}$H$_{19}$N$_9$O$_2$.0.2 C$_4$H$_8$O$_2$: C, 47.23; H, 5.92; N, 35.92; Found: C, 47.24; H, 5.92; N, 35.84.

EXAMPLE 13

2-Amino-9-(3-azido-2,3-dideoxy-β-D-erythro-pentofuranosyl)-6- ethylamino-9H-purine 2-Amino-9-(3-azido-2,3-dideoxy-β-D-erythro-pentofuranosyl)-6-chloro-9H-purine (0.23 g, 0.74 mmol) was dissolved in 20 mL anhydrous acetonitrile in a sealed tube. The solution was cooled to 0° C., saturated with ethylamine (Aldrich, lot #00115JV) and sealed. After heating at 70° C. for 16 hours, the reaction mixture was filtered and the filtrate evaporated to dryness. The residue was preloaded onto silica gel and eluted from a silica column using CHCl$_3$/MeOH (95:5, v/v). Combination and evaporation of appropriate fractions yielded 0.140 g (0.44 mmol, 59%) of product. mp=199°–201° C.

UV: pH 1 $\lambda max$ = 291, 255 ($\epsilon$ = 11500, 11600),
$\lambda min$ = 272, 238 ($\epsilon$ = 7700, 7300),
pH 13 $\lambda max$ = 281 ($\epsilon$ = 13800), $\lambda min$ 243 ($\epsilon$ = 6300),
$\lambda sh$ = 267 ($\epsilon$ = 10600)

$^1$H NMR (DMSO-$d_6$) δ 7.91 (s, 1H, H8), 6.12 (t, J=6.61 Hz, 1H, H1'), 5.85 (br s, 2H, NH$_2$), 5.35 (t, J=5.77 Hz, 1H, 5'OH), 4.61–4.57 (m, 1H, H3'), 3.92–3.87 (m, 1H', H4'), 3.61–3.38 (m, 4H, H5', NCH$_2$), 2.89–2.79 (m, 1H, H2'), 2.44–2.36 (m, 1H, H2'), 1.13 (t, 3H, CH$_3$)

Calcd. for C$_{12}$H$_{17}$N$_9$O$_2$: C, 45.14; H, 5.37; N, 39.48; Found: C, 45.20; H, 5.40; N, 39.43.

EXAMPLE 14

2-Amino-9-(3-azido-2,3-dideoxy-β-D-erythro-pentofuranosyl)-6-(cyclobutylamino)-9H-purine 2-Amino-9-(3-azido-2,3-dideoxy-β-D-erythro-pentofuranosyl)-6-chloro-9H-purine (0.24 g, 0.77 mmol) was reacted with cyclobutylamine (Aldrich, lot #00112KV, 0.55 g, 7.7 mmol) in 50 mL anhydrous acetonitrile for 16 hours at 75° C. The solvents were removed in vacuo and the residue preloaded onto silica gel. Elution from a silica column with CHCl$_3$/MeOH (95:5, v/v) followed by combination and evaporation of product containing fractions gave 0.17 g of impure material. The impure product was chromatographed on basic alumina with CHCl$_3$/MeOH (19:1, v/v) as the eluting solvent. Evaporation of product fractions yielded an oil; coevaporation with EtOAc gave a foam, 0.058 g (0.15 mmol, 19%). mp=139°–142° C.

UV: pH 1 $\lambda max$ = 295, 256 ($\epsilon$ = 12300, 11000),
$\lambda min$ = 273, 239 ($\epsilon$ = 7000, 6900),
pH 13 $\lambda max$ = 283 ($\epsilon$ = 14500), $\lambda min$ 245 ($\epsilon$ = 6900),
$\lambda sh$ = 262 ($\epsilon$ = 9700)

$^1$H NMR (DMSO-$d_6$) δ 7.92 (s, 1H, H8), 7.53 (br s, 1H, NH), 6.10 (t, J=6.49 Hz, 1H, H1') 5.84 (br s, 2H, NH$_2$), 5.31 (t, J=5.51 Hz, 1H, 5OH), 4.80–4.54 (m, 2H, H3', NCH), 3.89–3.84 (m, 1H, H4'), 3.60–3.50 (m, 2H, H5') 2.85–2.75 (m, 1H, H2'), 2.48–2.34 (m, 1H, H2'), 2.30–1.95 (m, 4H, 2 CH$_2$), 1.70–1.50 (m, 2H, CH$_2$).

Calcd. for C$_{14}$H$_{19}$N$_9$O$_2$·0.35 C$_4$H$_8$O$_2$·0.35 HCl: C, 47.55; H, 5.74; N, 32.41; Found: C, 47.51; H, 5.51; N, 32.46.

EXAMPLE 15 a) 2-Amino-6-(cyclopropylmethylamino)-9H-purine

2-Amino-6-chloropurine (Sigma, lot #69F4064, 11.2 g, 66.0 mmol) was suspended in 100 mL anhydrous acetonitrile containing triethylamine (9.2 mL, 66.0 mmol). N-Methylcyclopropylamine (Aldrich, 7.0 g, 98.4 mmol) was added and the reaction stirred at 70° C. for 24 hours and then at 85° C. for 16 hours. The reaction was filtered and the filtrate evaporated to dryness. The residue was preloaded onto silica gel and eluted from a silica column with EtOAc/MeOH (4:1, v/v). The fractions containing product were combined and evaporated. The residue was slurried in water, filtered, and dried to yield 2.36 g (10.9 mmol, 17%). mp =199° C.

UV: pH 1 λmax = 286, 257 (ε = 13600, 12900),
λmin = 270, 241 (ε = 10100, 8400)
pH 13 λmax = 293 (ε = 12900), λmin = 264 (ε = 4000).

$^1$H NMR (DMSO-d$_6$) δ 12.07 (br s, 1H, NH), 7.64 (s, 1H, H8), 5.63 (s, 2H, NH$_2$), 3.25–3.17 (m, 4H, NCH$_3$, NCH), 0.84–0.61 (m, 4H, 2 CH$_2$).

Calcd. for C$_9$H$_{12}$N$_6$·0.25 HCl·0.15 H$_2$O: C, 50.03; H, 5.85; N, 38.90; Found: C, 50.28; H, 5.71; N, 38.72.

b) 2-Amino-9-(3-azido-2,3-dideoxy-β-D-erythro-pentofuranosyl)-6-(cyclopropylmethylamino)-9H-purine To 800 mL of an aqueous pH 6.0, 50 mM citrate buffer, prepared as described in Example 2c, was added 2-amino-6-(cyclopropylmethylamino)-9H-purine (0.204 g, 0.8 mmol) and 3'-azido-3'-deoxythymidine (1.069 g, 4.0 mmol). Solution was achieved by heating the mixture at 50° C. with sonication. A sample was removed as a control. A 40 mL solution of trans-N-deoxyribosylase (Example 2b) with an activity of 1500 units/mL was added. The reaction was heated at 50° C. Six days later, 0.204 g, 0.8 mmol, of 2-amino-6-cyclopropylmethylpurine was added to the reaction. Twenty-one days after the reaction was started, another 0.204 g, 0.8 mmol, of 2-amino-6-cyclopropylpurine and 0.428 g, 1.6 mmol, of 3'-azido-3'-deoxythymidine were added to the reaction. The reaction was stopped after thirty-three days by heating to 80° C. to precipitate the enzyme. The aqueous solution was extracted with ethyl acetate to remove the product. The combined ethyl acetate fractions were dried with magnesium sulfate, filtered and the solvent was removed in vacuo to give a foam. The foam was chromatographed on basic alumina grade 1 eluted with chloroform/methanol (97:3, v/v). The product containing fractions were combined and the solvent was removed in vacuo to give the product as a foam 0.237 g, 29% yield. mp=104°–106° C.

UV: pH 1 λmax = 303, 256 (ε = 16600, 13100),
λmin = 275, 239 (ε = 5800, 8200)
pH 13 λmax = 287, 264, 299 (ε = 23100, 14400, 28700),
λmin = 268, 250 (ε = 14200, 12400), $^1$H NMR (DMSO-d$_6$) δ 7.96 (s, 1H, H8), 6.16 (t, J=6.58 Hz, 1H. H1'), 5.89 (s, 2H, NH$_2$), 5.28 (s, 1H, 5'OH), 4.63–4.58 (m, 1H, H3'), 3.92–3.88 (m, 1H, H4'), 3.62–3.58 (m, 2H, H5'), 3.24–3.21 (m, 4H, NH, NCH$_3$), 2.88–2.80 (m, 1H, H2'), 2.46–2.38 (m, 1H, H2'), 0.85–0.65 (m, 4H, 2 CH$_2$).

Calcd. for C$_{14}$H$_{19}$N$_9$O$_2$: C, 48.69; H, 5.55; N, 36.50; Found: C, 48.82; H, 5.56; N, 36.39.

EXAMPLE 16 a) 2-Amino-6-butoxy-9H-purine

The title compound was prepared in a manner analogous to the preparation of the compound of Example 11a, using 2-amino-6-chloropurine (Sigma, lot #69F4064, 4.4 g, 25.9 mmol) and sodium (Aldrich, lot #9621CL, 3 g, 129.5 mmol) in 250 mL n-butanol to give 4.4 g (21.2 mmol, 82%). mp=165° C.

UV: pH 1 λmax = 286 (ε = 11700), λmin = 252 (ε = 2100)
pH 13 λmax = 283 (ε = 8100), λmin = 258 (ε = 3400), $^1$H NMR (DMSO-d$_6$) δ 12.36 (br s, 1H, H9), 7.77 (s, 1H, H8), 6.19 (s, 2H, NH$_2$), 4.37 (t, J=6.64 Hz, 2H, OCH$_2$), 1.79–1.65 (m, 2H, CH$_2$), 1.50–1.32 (m, 2H, CH$_2$), 0.92 (t, J=7.22 Hz, 3H, CH$_3$).

Calcd. for C$_9$H$_{13}$N$_5$·0.3 H$_2$O: C, 50.84; H, 6.45; N, 32.94; Found: C, 50.88; H, 6.23; N, 32.93.

b) 2-Amino-9-(3-azido-2,3-dideoxy-β-D-erythro-pentofuranosyl)-6- butoxy-9H-purine 2-Amino-9-(3-azido-2,3-dideoxy-β-D-erythro-pentofuranosyl)-6- butoxy-9H-purine was prepared in a manner analogous to the preparation of 2-amino-9-(3-azido-2,3-dideoxy-β-D-erythropentofuranosyl)-6-(cyclobutoxy)-9H-purine (Example 18b). The product was chromatographed on basic alumina grade 1 eluted with chloroform/methanol (95:5, v/v). The fractions containing product were combined and the solvent removed in vacuo to give the product as a foam, 0.53 g, in 48% yield.

UV: pH 1 λmax = 285 (ε = 11900), λmin = 253 (ε = 3200)
pH 13 λmax = 279 (ε = 8300), λmin = 261 (ε = 4500),
λmax = 246 (ε = 8600)

$^1$H NMR (DMSO-d$_6$) δ 8.07 (s, 1H, 8H), 6.44 (s, 2H, 2NH$_2$), 6.14 (t, J=6.29 Hz, 1H, 1'H), 5.13 (t, J=5.47 Hz, 1H, 5'OH), 4.63–4.55 (m, 1H, 3'H), 4.38 (t, 2H, OCH$_2$), 3.90–3.84 (m, 1H, 4'H), 3.58–3.53 (m, 2H, 5'H), 2.89–2.76 and 2.49–2.36 (m, 2H, 2'H), 1.79–1.64 (m, 2H, CH$_2$), 1.49–1.31 (m, 2H, CH2), 0.92 (t, 3H, CH$_3$).

Calcd for C$_{14}$H$_{20}$N$_8$O$_3$: C, 48.27; H, 5.79; N, 32.17; Found: C, 48.26; H, 5.79; N, 32.11.

EXAMPLE 17 a) 2-Amino-6-phenoxy-9H-purine

Potassium t-butoxide (J. T. Baker, 7.3 g, 64.8 mmol) was added to a solution of phenol (Mallinckrodt, 15.2 g, 162 mmol) in 50 mL anhydrous DMSO. After stirring for 30 minutes, 2-amino-6-chloropurine (Sigma, lot #69F4064. 5.5 g, 32.4 mmol) was added and the mixture stirred for 6 days at 100° C. The reaction was poured onto ice and extracted with EtOAc. The solvents were removed in vacuo and the resultant oil applied to a silica gel column. Elution with CHCl$_3$/MeOH (95:5, v/v) followed by combination and evaporation of appropriate fractions gave 1.6 g (7.0 mmol, 22%) of product. mp=228° C.

UV:  pH 1 λmax = 292 (ε = 11900), λmin = 256 (ε = 2400)
     pH 13 λmax = 289 (ε = 8700), λmin = 260 (ε = 3500).

$^1$H NMR (DMSO-d$_6$) δ 7.93 (s, 1H, H8), 7.46–7.19 (m, 5H, phenyl), 6.22 (s, 2H, NH$_2$).

Calcd. for C$_{11}$H$_9$N$_5$O: C, 58.14; H, 3.99; N, 30.82; Found: C, 58.04; H, 4.01; N, 30.77.

b) 2-Amino-9-(3-azido-2,3-dideoxy-β-D-erythro-pentofuranosyl)-6-phenoxy-9H-purine To 800 mL of an aqueous pH 6.0, 50 mm citrate buffer, prepared as described in Example 2c' was added 2-amino-6-phenoxy-9H-purine (0.181 g, 0.8 mmol) and 3'-azido-3'-deoxythymidine (1.069 g, 4.0 mmol). Solution was achieved by heating the mixture at 50° C. with sonication. A sample was removed as a control. A 40 mL solution of trans-N-deoxyribosylase (Example 2b) with an activity of 1500 units/mL was added. The reaction was heated at 50° C. Six days later, 0.181 g, 0.8 mmol, of 2-amino-6-phenoxypurine was added to the reaction. Fifteen days after the reaction was started, another 0.181 g, 0.8 mmol, of 2-amino-6-phenoxypurine and 0.428 g, 1.6 mmol, of 3'-azido-3'-deoxythymidine were added to the reaction. The reaction was stopped after thirty-three days, by heating to 80° C. to precipitate the enzyme, and filtered. The aqueous solution was extracted with ethyl acetate to remove the product. The combined ethyl acetate fractions were dried with magnesium sulfate, filtered and the solvent removed in vacuo to give a foam. The foam was chromatographed on basic alumina grade 1 eluted with chloroform/methanol (99:1, v/v). The fractions containing product were combined and the solvent removed in vacuo to give the product as a foam, 0.48 g, 54% yield.

UV:  pH 1 λmax = 293 (ε = 10300), λmin = 263 (ε = 3830),
     λmax = 243 (ε = 8880)
     pH 13 λmax = 286 (ε = 13500), λmin = 263 (ε = 5850),
     λmax = 246 (ε = 12900)

$^1$H NMR (DMSO-d$_6$) δ 8.22 (s, 1H, 8H), 7.5–7.2 (m, 5H, phenyl), 6.5 (s, 2H, 2NH$_2$), 6.20 (t, J=6.34 Hz, 1H, 1'H), 5.15 (s, 1H, 5'OH), 4.7–4.6 (m, 1H, 3'H), 3.95–3.85 (m, 1H, 4'H), 3.65–3.50 (m, 2H, 5'H), 2.9–2.8 (m, 1H, 2'H), 2.5–2.4 (m, 1H, 2'H, obscured by DMSO).

Calcd. for C$_{16}$H$_{16}$N$_8$O$_3$: C, 52.17; H, 4.38; N, 30.42; Found: C, 52.22; H, 4.39; N, 30.35.

EXAMPLE 18 a) 2-Amino-6-cylcobutoxy-9H-purine

Sodium (Aldrich, lot #9621CL, 4.1 g, 176.9 mmol) was added to 250 mL acetonitrile containing cyclobutanol (Aldrich, 4.6 g, 63.7 mmol). Following reaction of sodium with the cyclobutanol, 2-amino-6-chloropurine (Sigma, lot #69F4046, 6.0 g, 35.4 mmol) was added, and the mixture was heated at 70° C. for 18 hours. The solvents were decanted off, and water was added to the residue. The pH was adjusted to 7 with 1N HCl to give a precipitate. The precipitate was filtered, washed with water, then dried to give 4.5 g (21.7 mmol, 62%) of product, mp=218° C. (dec).

UV:  pH 1 λmax = 284 (ε = 7800), λmin = 258 (ε = 3500),
     pH 13 λmax = 285 (ε = 10300), λmin = 252 (ε = 2400)

$^1$H NMR (DMSO-d$_6$) δ 12.36 (s, 1H, NH), 7.78 (s, 1H, H8), 6.14 (s, 2H, NH$_2$), 5.4–5.2 (m, 1H, OCH), 2.45–1.50 (m, 6H, cyclobutyl).

Calcd. for C$_9$H$_{11}$N$_5$O·0.1 H$_2$O: C, 52.22; H, 5.45; N, 33.83; Found: C, 52.13; H, 5.48; N, 33.55.

b) 2-Amino-9-(3-azido-2,3-dideoxy-β-D-erythro-pentofuranosyl)-6-(cyclobutoxy)-9H-purine To 800 mL of an aqueous pH 6.0, 50 mM citrate buffer, prepared as described in Example 2c, was added 2-amino-6-(cyclobutoxy)-9H-purine (0.164 g, 0.8 mmol) and 3'-azido-3'-deoxythymidine (1.069 g, 4.0 mmol). Solution was achieved by heating the mixture at 50° C. with sonication. A sample was removed as a control. A 40 mL solution of trans-N-deoxyribosylase with an activity of 1500 units/mL was added. The reaction was heated at 50° C. Five days later 0.164 g, 0.8 mmol, of 2-amino-6-cyclobutoxypurine was added to the reaction. Ten days after the reaction was started, another 0.164 g, 0.8 mmol, of 2-amino-6-cyclobutoxypurine and 0.428 g, 1.6 mmol, of 3'-azido-3'-deoxythymidine were added to the reaction. Twenty-one days after the reaction was started, 0.164 g, 0.8 mmol, of 2-amino-6-cyclobutoxypurine was added to the reaction. The reaction was stopped after twenty-six days by heating to 80° C. to precipitate the enzyme. After chilling to 0° C. the mixture was filtered. The aqueous filtrate was extracted with ethyl acetate (3 times) to remove the product. The combined ethyl acetate fractions were dried with magnesium sulfate, filtered and the solvent removed in vacuo to give a foam. The foam was chromatographed on basic alumina grade 1 eluted with chloroform/methanol (95.5, v/v). The product containing fractions were combined and the solvent removed in vacuo to give the product as a foam, 0.334 g, in 32% yield.

UV:  pH 1 λmax = 288 (ε = 10000), λmin = 261 (ε = 3500),
     λsh = 243 (ε = 7100)
     pH 13 λmax = 281 (ε = 11000), λmin = 261 (ε = 6500),
     λsh = 247 (ε = 10600)

$^1$H NMR (DMSO-d$_6$) δ 8.06 (s, 1H, 8H), 6.4 (br s, 2H, 2NH$_2$), 6.14 (t, J=6.44 Hz, 1H, 1'H), 5.35–5.2 (m, 1H, CH), 5.14 (t, J=5.6 Hz, 1H, 5'OH), 4.6–4.5 (m, 1H, 3'H), 3.9–3.8 (m, 1H, 4'H), 3.6–3.50 (m, 2H, 5'H), 2.89–2.76 and 2.5–2.34 (m, 2H, 2'H), 2.20–2.00 (m, 2H, CH$_2$), 1.9–1.6 (m, 2H, CH$_2$).

Calcd. for C$_{13}$H$_{18}$N$_8$O$_3$: C, 48.55; H, 5.24; N, 32.35; Found: C, 48.75; H, 5.25; N, 32.20.

EXAMPLE 19 a) 2-Amino-6-methylpropylamino-9H-purine

2-Amino-6-chloropurine (Sigma, lot #69F4064, 6.0 g, 35.4 mmol) was suspended in 75mL acetonitrile. N-Methylpropylamine (Aldrich, lot #00923AW. 10.0 g, 136.7 mmol) was added and the reaction stirred at 75° C. for 24 hours. The solvents were evaporated to give an oil. Stirring the oil with water yielded a solid which was filtered and dried to give 5.9 g (28.6 mmol, 81%); mp=181°C.

UV:  pH 1 λmax = 283 (ε = 14300), λmin = 270 (ε = 10800),
     λsh = 256 (ε = 12800),
     pH 13 λmax = 290 (ε = 13500), λmin = 261 (ε = 4700);

¹H NMR (DMSO-d₆) δ 12.0 (s,1H,NH), 7.6 (s,1H,H8), 5.6 (s,2H,NH₂), 4.0 (br s,2H,NCH₂), 3.2 (s,3H,NCH₃), 1.7-1.5 (m,2H,CH2), 0.9 (t, J=7.3 Hz,3H,CH₃).

Calcd. for C₉H₁₄N₆·0.15 CH₃CN: C,52.59, H, 6.86. N, 40.55; Found: C, 52.55, H, 6.88, N, 40.57.

b) 2-Amino-9-(3-azido-2,3-dideoxy-β-D-erythro-pentofuranosyl)-6-methylpropylamino-9H-purine The title compound was prepared in a manner analogous to the preparation of 2-amino-9-(3-azido-2,3-dideoxy-β-D-erythro-pento furanosyl)-6-cyclopropylmethylamino-9H-purine (Example 15b). The reaction was worked up in an analogous manner except the combined ethyl acetate fractions were back washed with 150mL of 1M potassium carbonate two time prior to chromatography. The product was isolated in 50% yield, 0.347 g. mp=101°-104° C.

UV:  pH 1 λmax = 295 (ε = 12600) λmin = 274 (ε = 8100)
     λmax = 257 (ε = 12300) λmin = 241 (ε = 8100)
     pH 13 λmax = 284 (ε = 16200) λmin = 249 (ε = 7700)

¹H NMR (DMSO-d₆) δ 7.93 (s,1H,H8), 6.13 (t,J=6.64 Hz,1H,H1'), 5.81 (s,2H,2NH₂), 5.27 (t,J=5.37 Hz,1H,5'OH), 4.61-4.53 (m,1H,H3'), 4.00-3.80 (m,3H,H4',NCH₂), 3.59-3.53 (m,2H,H5'), 3.23 (br s'3H,CH₃), 2.87-2.73 (m,1H,H2'), 2.45-2.32 (m,1H,H2'), 1.64-1.53 (m,2H,CH2), 0.84 (t,J=7.37 Hz,3H'CH₃).

Calcd: C₁₄H₂₁N₉O₂ C, 48.41, H, 6.09, N, 36.29; Found: C, 48.65, H, 6.14, N, 36.37.

EXAMPLE 20 a) 2-Amino-6-azetidinyl-9-H-purine

2-Amino-6-chloropurine (Sigma, lot #69F4064, 1.0 g, 5.8 mmol) was suspended in 50mL acetonitrile. Azetidine (Aldrich, lot #05606HV, 1.0 g, 17.5 mmol) was added and the reaction stirred at 62° C. for 24 hours. The solvents were evaporated to give a white solid which was recrystallized from methanol to yield 0.71 g (3.7 mmol, 65%); mp=280° C.

UV pH 1 λmax = 283, 253 (ε = 13300, 12300)
   λmin = 267, 241 (ε = 8900, 10000)
   λsh = 293 (ε = 12300),
   pH 13 λmax = 292 (ε = 13400) λmin = 261 (ε = 4300)

¹H NMR (DMSO-d₆) δ 12.07 (br s,1H,NH) 7.62 (s,1H,H8), 5.74 (s,2H,NH₂), 4.36-4.09 (br m,4H,N(CH₂)₂), 2.42-2.27 (m,2H,CH₂).

Calcd. for C₈H₁₀N₆ 0.55 H₂O: C,48.02, H,5.59, N,42.00; Found: C,47.77, H,5.25, N,4.19.

b) 2-Amino-6-(1-azetidinyl)-9-(3-azido-2,3-dideoxy-β-D-erythropentofuranosyl)-9H-purine The title compound was prepared in a manner analogous to the preparation of 2-amino-9-(3-azido-2,3-dideoxy-β-D-erythropentofuranosyl)-6-cyclopropylmethylamino-9H-purine (Example 15b). The reaction was worked up in an analogous manner except the combined ethyl acetate fractions were back washed with 150 mL of 1M potassium carbonate two times prior to chromatography. The product was isolated in 56% yield, 0.373 g, mp.=141°-143°C.

UV pH 1 λmax = 298 (ε = 15900) λmin = 274 (ε = 8800)
   λmax = 257 (ε = 14000) λmin = 238 (ε = 7700)
   pH 13 λmax = 285 (ε = 17400) λmin = 247 (ε = 8600)

¹H NMR (DMSO-d₆) δ 7.89 (s, 1H,H8), 6.10 (t,J=6.64 Hz,1H,H1'), 5.93 (s,2H,2NH₂), 5.26 (t,J=5.62 Hz,1H,5'OH), 4.61-4.53 (m,1H,H3'), 4.23 (br s,4H,2CH2), 3.90-3.84 (m,1H,H4'), 3.61-3.52 (m,2H,H5'), δ 2.87-2.74 (m,1H,H2'), 2.44-2.28 (m,1H,H2').

Calcd.: for C₁₃H₁₇N₉O₂, C,47.13, H,5.17, N,38.05;Found: C,47.24, H,5.21. N,37.96.

EXAMPLE 21 a) 2-Amino-6-ethylmethylamino-9-H-purine

2-Amino-6-chloropurine (Sigma, lot #69F4064, 6.5g, 38.3 mmol) was suspended in 75mL acetonitrile. N-Ethylmethylamine (6.8 g, 115.0 mmol) was added and the reaction stirred at 75° C. for 24 hours. The solvents were evaporated to give a solid which was slurried in H₂O, filtered, and air dried to yield 4.86g (25.3 mmol, 66%); mp=206°C.

UV pH 1 λmax = 283 (ε = 14800) λmin = 266 (ε = 10900)
   λsh = 255 (ε = 13400)
   pH 13 λmax = 290 (ε = 13700) λmin = 261 (ε = 4900)

¹H NMR )DMSO-d₆) δ 12.1 (br, s1H,H9), 7.6 (s,1H,H8), 5.6 (s,2H,NH₂), 4.0-3.9 (br d,2H,NCH₂), 3.4-3.2 (m,3H,NCH₃), 1.1-1.0 (m,3H,CH₃).

Calcd. for C₈H₁₂N₆: C,49.98, H,6.59, N,43.72;Found: C,50.04, H,6.57. N,43.64.

b) 2-Amino-9-(3-azido-2,3-dideoxy-β-D-erythro-pentofuranosyl)-6-ethylmethylamino-9H-purine The title compound was prepared in a manner analogous to the preparation of 2-amino-9-(3-azido-2,3-dideoxy-β-D-erythropentofuranosyl)-6-cyclopropylmethylamino-9H-purine (Example 15b). The reaction was worked up in an analogous manner except the combined ethyl acetate fractions were back washed with 150 mL of 1M potassium carbonate two times prior to chromatography. The product was isolated in 54% yield, 0.362 g, mp=38°-43° C.

UV (nm) pH 1 λmax 295 (ε = 13200) λmin 274 (ε = 8600)
        λmax 257 (ε = 13100) λmin 240 (ε = 8300)
        pH 13 λmax 284 (ε = 16600) λmin 248 (ε = 7900)

¹H NMR (DMSO-d6) δ 7.93 (s,1H,H8), 6.13 (t,J=6.59 Hz,1H,H1'), 5.82 (s,2H,2NH₂), 5.27 (t,J=5.37 Hz,1H,5'OH). 4.61-4.53 (m,1H,H3'), 4.05-3.84 (m,3H,H4',NCH₂), δ 3.59-3.53 (m,2H,H5'), δ 3.25 (br s,3H,CH₃) 2.87-2.74 (m,1H,H2'), 2.47-2.33 (m,1H,H2'), 1.11 (t,J=7.04 Hz,3H,CH3).

Calcd. for C₁₃H₂₁N₉O₂ C,46.84, H,5.74, N,37.82; Found: C,46.57, H,5.79, N,37.65.

EXAMPLE 22 a) 2-Amino-6-pyrrolidinyl-9-H-purine

2-Amino-6-chloropurine (Sigma, lot #69F4064, 5.0 g, 29.5 mmol) was stirred in pyrrolidine (Kodak, lot #B161, 30mL) at 80° C. for 24 hours. The solvent was evaporated to a gold solid which was recrystalized from methanol to yield 3.41 g (16.7 mmol, 58%); mp=265°C.

UV pH 1 λmax = 283, 255 (ε = 13000, 11900)
λmin = 267, 241 (ε = 9100, 9300)
λsh = 290 (ε = 12100)
pH 13 λmax = 291 (ε = 14200) λmin = 258 (ε = 5000)

$^1$H NMR (DMSO-d$_6$) δ 12.08 (s,1H,NH), 7.62 (s,1H,H8), 5.63 (s,2H,NH$_2$), 4.1–3.4 (br m,4H′N(CH$_2$)$_2$).
Calcd. for C$_9$H$_{12}$N$_6$·0.35 H$_2$O ·0.0.5 CH$_3$OH: C,50.36, H,6.54, N,37.09; Found: C, 50.32, H,6.54, N,37.09.

b) 2-Amino-9-(3-azido-2,3-dideoxy-β-D-erythro-pentofuranosyl)-6-pyrrolidinyl-9H-purine The title compound was prepared in a manner analogous to the preparation of 2-Amino-9-(3-azido-2,3-dideoxy-β-D-erythropentofuranosyl)-6-cyclopropylmethylamino-9H-purine (Example 15b). The reaction was worked up in an analogous manner except the combined ethyl acetate fractions were back washed with 150 mL of 1M potassium carbonate two times prior to chromatography. The product was isolated in 52% yield, 0.360 g, mp=180°–183°C.

UV pH 1 λmax = 298 (ε = 17800) λmin = 275 (ε = 9600)
λmax = 257 (ε = 15500) λmin = 237 (ε = 8100)
pH 13 λmax = 284 (ε = 20000) λmin = 247 (ε = 9000)

$^1$H NMR (DMSO-d$_6$) δ 7.90 (s,1H,H8), 6 12 (t,J=6.64 Hz,1H,H1′), 5.81 (s,2H,NH$_2$), 5.30 (t,J=5.63 Hz,1H,5′OH), 4.60–4.52 (m,1H,H3′), 4.00–3.45 (m,7H,H4′,H5′,2CH2), δ 2.90–2.73 (m,1H,H2′), 2.44–2.35 (m,1H,H2′), 1.88 (br s,4H,2CH$_2$).
Calcd. for C$_{14}$H$_{19}$N$_9$O$_2$: C,48.69, H,5.54, N,36.50; Found: C,48.95. H,5.59, N,36.31.

EXAMPLE 23

2-Amino-9-(3-azido-2,3-dideoxy-β-D-erythro-pentofuranosyl)-6-(n-butylamino)-9-H-purine 2-Amino-9-(3-azido-2,3-dideoxy-β-D-erythro-pentofuranosyl)-6-chloro-9H-purine (Example 3d) (0.40 g, 1.29 mmol) and n-butylamine (Aldrich, #06221JP, 1.28mL, 12.9 mmol) were combined in 25 mL MeOH and placed in a sealed tube. The reaction was heated at 60° C. for 18 hours followed by evaporation of the solvents. Chromatography of the residue on basic alumina eluted with 2% MeOH in CHCl$_3$ gave, after combination and evaporation of appropriate fractions, 0.279 g (0.8 mMol. 62.3%); mp=44°–47°C.

UV pH 1 λmax = 295, 253 (ε = 14500, 13600)
λmin = 272, 237 (ε = 8200, 9000)
pH 13 λmax = 281 (ε = 14300) λmin = 242 (ε = 6200)
λsh = 264 (ε = 10500)

$^1$H NMR (DMSO-d$_6$) δ 7.89 (s,1H,H8), 7.20 (br s,1H,NH), 6.10 (t,J=6.44 Hz,1H,H1′), 5.80 (s,2H,NH$_2$), 5.32 (t,J=5.47 Hz,1H,5′OH), 4.61–4.52 (m,1H,H3′), 3.90–3.85 (m,1H,H4′), 3.60–3.30 (m,4H,H5′,CH$_2$), 2.90–2.75 (m,1H,H2′), 2.47–2.30 (m,1H,H2′), 1.60–1.20 (m,4H,2CH$_2$), 0.87 (t,J=7.23 Hz,3H,CH$_3$).
Calcd. for C$_{14}$H$_{21}$N$_9$O$_2$: C,48.41, H,6.09, N,36.29; Found: C,48.16, H,6.07, N,36.05.

EXAMPLE 24

Trans-2-amino-9-(3-azido-2,3-dideoxy-β-D-erythro-pentofuranosyl)-6((2-phenylcyclopropyl)amino)-9H-purine Trans-2-phenylcyclopropylamine hydrochloride (Aldrich, lot #01903MK, 2.5 g, 14.7 mmol) was dissolved in 5 mL H$_2$O and the pH adjusted to pH 12. The aqueous solution was extracted with 10 mL EtOAc. The EtOAc was evaporated to dryness and dissolved in 25 mL EtOH. 2-Amino-9-(3-azido-2,3-dideoxy-β-D-erythro-pentofuranosyl)-6-chloro-9H-purine (Example 3d) (0.4 g, 1.29 mmol) was added to the ethanolic solution then placed in a sealed tube and heated at 50° C. for 18 hours. The solvents were removed in vacuo to yield a dark oil. The oil was chromatographed on basic alumina eluted with 1% MeOH in CHCl$_3$. The impure product fractions were combined, evaporated, and re-chromatographed on silica gel eluted with 5% MeOH in CHCl$_3$. The collected impure product was again applied to basic alumina eluted with 1% MeOH in CHCl$_3$ to give, after combination and evaporation of appropriate fractions, 0.0802 g (0.2 mMol, 15.5%); mp=65°–70°C.

UV pH 1 λmax = 297, 253 (ε = 15500, 13000)
λmin = 273, 247 (ε = 7800, 12600)
pH 13 λmax = 285, 260 (ε = 21700, 14000)
λmin = 265. 254 (ε = 13800, 13600)

$^1$H NMR (DMSO-d$_6$) δ 7.92 (s,1H,H8), 7.62 (br d,J=5.47 Hz,1H,NH), 7.30–7.10 (m,5H,phenyl), 6.11 (t,J=6.53 Hz,1H,H1′), 5.82 (s,2H NH$_2$), 5.28 (t,J=5.70 Hz,1H,5′H), 4.60–4.50 (m,1H,H3′), 3.89–3.82 (m′,1H,H4′), 3.59–3.53 (m,2H,H5′) 2.90–2.79 (m,1H,H2′), 2.50–2.36 (m,1H,H2′), 2.20–2.08 (m,1H,CH), 1.40–1.15 (m,2H,CH2).
Calcd for C$_{19}$H$_{21}$N$_9$O$_2$·0.75 MeOH: C,54.98, H,5.61, N,29.22; Found: C,55.34. H,5.30, N,28.82,

EXAMPLE 25

2-Amino-9-(3-azido-2,3-dideoxy-β-D-erythro-pentofuranoysl)-6(2-phenethylamino)-9-H-purine 2-Amino-9-(3-azido-2,3-dideoxy-β-D-erythro-pentofuranoysl)-6-chloro-9-H-purine (Example 3d) (0.40 g, 1.3 mmol) and phenethylamine (Aldrich, lot #06410LP, 0.79g, 6.5 mMol) were refluxed in 15 mL MeOH for 18 hours. The solvents were evaporated and the residue chromatographed on basic alumina eluted with 5% MeOH in CHCl$_3$. The product fractions were combined and evaporated to give 0.49g (1.15 mmol, 96%); mp=89°–92°C.

UV (nm) pH 1 λmax = 292 (ε = 14400)
λmin = 272 (ε = 10200)
λsh = 254 (ε = 14700)
pH 13 λmax = 282 (ε = 18800)
λmin = 244 (ε = 9400)
λsh = 263 (ε = 13500)

$^1$H NMR (DMSO-d$_6$) δ 7.9 (s,1H,H8), 7.4–7.1 (m,6H,NH,phenyl), 6.1 (t,J=6.6 Hz,1H,H1'), 5.8 (br s,2H,NH$_2$), 5.3 (t,J=5.8 Hz,1H,5'OH), 4.6–4.5 (m,1H,H3'), 3.9–3.8 (m,1H,H4'), 3.6–3.5 (m,4H,H5',CH$_2$), 2.9–2.7 (m,3H,H2',CH$_2$), 2.4–2.3 (m,1H,H2').

Calcd. for C$_{18}$H$_{21}$N$_9$O$_2$·0.3 EtOAc·0.2 H$_2$O; C,54.20, H,5.64, N,29.63; Found: C, 54.23, H, 5.60, N, 29.63.

EXAMPLE 26

2-Amino-9-(3-azido-2,3-dideoxy-β-D-erythro-pentofuranosyl)-6-(cyclopropylmethylamino)-9H-purine 5'-phosphate 2-Amino-9-(3-azido-2,3-dideoxy-β-D-erythro-pentofuranosyl)-6-cyclopropylmethylamino-9H-purine (Example 15b) (0.050 g, 0.14 mmol) was dissolved in 1.25 mL of 1,3 dimethyl-3,4,5,6-tetrahydo-2(1H)-pyrimidinone (Aldrich lot #01812AX). The solvent was dried by standing over calcium hydride for twenty four hours. The solution was chilled in a −20° C. ice/methanol bath. Phosphorus oxychloride (0.054 mL, 0.58 mmol, 4 eq., Aldrich lot #00421TW) was added. After stirring for three minutes. 5 mL of water were added and the reaction stirred in a 0° C. ice water bath for thirty minutes. The reaction was neutralized to pH 7 by the addition of 1N sodium hydroxide. The Sephadex-DEAE (A-25) ion-exchange column in the ammonium bicarbonate was prepared by washing thirty five mLs of resin with 200 mL of 50 mmol ammonium bicarbonate. The aqueous reaction solution was loaded onto the column. The column was washed with 400 mL of 50 mmol ammonium bicarbonate to remove the inorganic salts. The column was washed with 100 mL of 100 mmol ammonium bicarbonate followed by 300 mL of 200 mmol ammonium bicarbonate. The product came off in the second 100 mL fraction of the 200 mmol ammonium bicarbonate wash. The water and some ammonium bicarbonate was removed by rotary evaporation in vacuo. The residue was dissolved in 10 mL of distilled water and rotary evaporated a second time. The final residue was dissolved in 20 mL of distilled water and freeze dried to give 0.042 g, 68% yield, of product as a white solid.

| | |
|---|---|
| UV (nm) pH 1 λmax = | 302 (ε = 15200) |
| λmin = | 275 (ε = 5400) |
| λmax = | 256 (ε = 12200) |
| λmin = | 238 (ε = 7600) |
| pH 13 λmax = | 286 (ε = 16800) |
| λmin = | 249 (ε = 8900) |

$^{13}$C-NMR (DMSO-d$_6$): NMR: δ 82.9 (4'C), 82.2 (1'C) 64.3 (5'C), 61.8 (3'C), 35.9 (2'C), 35.2 (6-NCH3), 32.6 (6-NcPrCH), 8.2 (6-NcPrCH2).

$^{31}$P-NMR taken in DMSO-d$_6$: 0.6 (5'P04): Calcd. for C$_{14}$H$_{20}$N$_9$O$_5$ P.0.5 NH$_3$ 1.45 H$_2$O C,36.56 H,5.35 N,28.93; Found C, 36.66 H,5.22, N,29.02.

EXAMPLE 27

Tablet Formulations

The following formulations A, B and C are prepared by wet granulation of the ingredients with a solution of povidone, followed by addition of magnesium stearate and compression.

| | | mg/tablet | mg/tablet |
|---|---|---|---|
| Formulation A | | | |
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
| | | 500 | 300 |
| Formulation B | | | |
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
| | | 500 | 300 |
| Formulation C | | | |
| Active ingredient | | | 100 |
| Lactose | | | 200 |
| Starch | | | 50 |
| Povidone | | | 5 |
| Magnesium Stearate | | | 4 |
| | | | 359 |

The following formulations, D and E, are prepared by direct compression of the admixed ingredients. The lactose in formulation E is of the direct compression type (Dairy Crest-"Zeparox").

| | mg/tablet |
|---|---|
| Formulation D | |
| Active ingredient | 250 |
| Pregelatinized Starch NF15 | 150 |
| | 400 |
| Formulation E | |
| Active ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | |
|---|---|
| (a) Active ingredient | 500 |
| (b) Hydroxypropylmethylcellulose (Methocel K4M Premium) | 112 |
| (c) Lactose B.P. | 53 |
| (d) Povidone B.P. | 28 |
| (e) Magnesium Stearate | 7 |
| | 700 |

Drug release takes place over a period of about 6–8 hours and is complete after 12 hours.

EXAMPLE 28

Capsule Formulations

Formulation A

A capsule formulation is prepared by admixing the ingredients of Formulation D in Example 2 above and filling into a two-part hard gelatin capsule. Formulation B (infra) is prepared in a similar manner.

Formulation B

| | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

Formulation C

| | mg/capsule |
|---|---|

| | |
|---|---|
| (a) Active ingredient | 250 |
| (b) Macrogol 4000 B.P. | 350 |
| | 600 |

Formulation D

| | mg/capsule |
|---|---|
| Active ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active ingredient | 250 |
| (b) Microcrystalline Cellulose | 125 |
| (c) Lactose B.P. | 125 |
| (d) Ethyl Cellulose | — |
| | 513 |

EXAMPLE 29

Injectable Formulation

Formulation A

| | |
|---|---|
| Active ingredient | 0.200 g |
| Hydrochloric acid solution, 0.1M, or | |
| Sodium hydroxide solution, 0.1M q.s. to Ph | 4.0 TO 7.0 |
| Sterile water | q.s. to 10 mL |

The active ingredient is dissolved in most of the water (35° C.–40° C.) and the pH adjusted to between 4.0 and 7.0 with the hydrochloric acid or the sodium hydroxide as appropriate. The batch is then made up to volume with the water and filtered through a sterile micropore filter into a sterile 10 mL amber glass vial (type 1) and sealed with sterile closures and overseals.

Formulation B

| | |
|---|---|
| Active ingredient | 0.125 |
| Sterile, pyrogen-free, pH 7 phosphate Buffer, | q.s. to 25 mL |

EXAMPLE 29

| Intramuscular injection | |
|---|---|
| Active ingredient | 0.20 g |
| Benzyl Alcohol | 0.10 g |
| Glycofurol 75 | 1.45 g |
| Water for Injection | q.s. to 3.00 mL |

The active ingredient is dissolved in the glycofurol. The benzyl alcohol is then added and dissolved, and water added to 3 mL. The mixture is then filtered through a sterile micropore filter and sealed in sterile 3 mL amber glass vials (type 1).

EXAMPLE 30

| Syrup | |
|---|---|
| Active ingredient | 0.25 g |
| Sorbitol Solution | 1.50 g |
| Glycerol | 2.00 g |
| Sodium Benzoate | 0.005 g |
| Flavor, Peach 17.42.3169 | 0.0125 mL |
| Purified Water | q.s. to 5.00 mL |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

Formulation B

| | |
|---|---|
| Active ingredient | 0.125 g |
| Sterile, pyrogen-free, pH 7 phosphate buffer, | q.s to 25 mL |

EXAMPLE 31

Suppository

| | mg/suppository |
|---|---|
| Active ingredient | 250 |
| Hard Fat, B.P. (Witepsol H15-Dynamit NoBel) | 1770 |
| | 2020 |

One-fifth of the Witepsol H15 is melted in a steam-jacketed pan at 45° C. maximum. The active ingredient is sifted through a 200M sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250M stainless steel screen and, with continuous stirring, is allowed to cool to 40° C. At a temperature of 38° C. to 40° C., 2.02 g of the mixture is filled into suitable, 2 mL plastic molds. The suppositories are allowed to cool to room temperature.

EXAMPLE 32

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 33

Antiviral testing a) Antiviral Activity Against Human Immunodeficiency Virus (HIV)

i) Anti-HIV activity was determined by measuring the ability of the compound to reverse the cytopathic effect of HIV infection. This was determined by a quantitative assessment of cell growth monitored at the fifth day post infection by a propidium iodide dye uptake test. MT4 cells were incubated with 100XTCID$_{50}$ of HIV-1 (strain 3B) or HIV-2 (Zagury strain) for one hour prior to addition of compound in six different concentrations varying from 2 to 200 μM. The cells were allowed to incubate for five days at 37° C. On day five, NP-40, a detergent, was added to a final concentration of 0.5% immediately prior to analysis. Cell number was determined using a method which measures the fluorescence of a dye (propidium iodide) which binds to DNA. Since the amount of DNA is directly proportional to cell number, this fluorescence assay is an indication of cell growth. While uninfected cells double in cell number several times during the five days duration of the assay, HIV-infected cells grow very little, if at all. A compound which reverses the cytopathic effect of HIV would allow for rapid cell growth, approaching that of the mock-infected cells.

The antiviral effect of a drug is reported as an $IC_{50}$, i.e., as the inhibitory concentration that would protect 50% of the cells from cell killing, measured as 50% of that cell growth determined for uninfected MT4 cell controls.

TABLE 1

| EXAMPLE | ANTI-HIV $IC_{50}$ | |
|---|---|---|
|  | HIV-1 | HIV-2 |
| 2-Amino-9-(3-azido-2,3-dideoxy-$\beta$-D-erythro-pentofuranosyl)-6-methoxy-9H-purine (Example 2c) | 5.6 $\mu$M<br>6.9 $\mu$M | 5.5 $\mu$M |
| 2-Amino-9-(3-azido-2,3-dideoxy-$\beta$-D-erythro-pentofuranosyl)-6-benzyloxy-9H-purine (Example 6b) | 8.9 $\mu$M |  |
| 2-Amino-9-(3-azido-2,3-dideoxy-$\beta$-D-erythro-pentofuranosyl)-6-dimethyl-amino-9H-purine (Example 7b) | 2.5 $\mu$M<br>20.9 $\mu$M |  |
| 3-Amino-9-(3-azido-2,3-dideoxy-$\beta$-D-erythro-pentofuranosyl)-6-(cyclopropylmethylamino)-9H-purine (Example 15b) | 1.6 $\mu$M<br>6.4 $\mu$M |  | ii) Anti-HIV activity was also determined by measuring the presence of reverse transcriptase (RT) in the media Since the amount of RT present in the cell-free supernatant is directly proportional to the number of virus particles released by the infected cells, a reduction in RT is indicative of a reduction in virus production. MT4 cells were infected with HIV-1 or HIV-2 prior to the addition of compound in six different concentrations varying from 2 to 200M as above reverse transcriptase (RT) was measured by assaying the cell-free supernatant after five days incubation of HIV-infected MT4 cells. A 50 $\mu$l sample of supernatant was disrupted by the addition of 10 $\mu$L of the following mixture:

| |
|---|
| 0.5M KCl |
| 50 mM DTT |
| 0.5% Triton X-100 |

After 5 minutes incubation to allow for disruption of the virus, the following reagents were added to the assay:

| | |
|---|---|
| 10 $\mu$L | 5 mM EGTA in 0.5M Tris HCl, pH 7.8 |
| 1 $\mu$L | 0.5M MgCl$_2$ |
| 3 $\mu$L | 3H-dTTP |
| 10 $\mu$L | poly rA-odT (2.5 OD/ml) |
| 16 $\mu$L | water |

The assays were allowed to incubate for two hours before being spotted onto DEAE paper. The DEAE paper was washed four times (10 minutes each) with 5% sodium phosphate (dibasic) and two times with 95% EtOH prior to counting in a scintillation counter. The antiviral effect of the drug is reported as an $IC_{50}$, i.e., the inhibitory concentration that results in a 50% reduction of RT as compared to infected control cells.

The compound of Example 2c, 2-amino-9-(3-azido-2,3-dideoxy-D-erythro-pento-furanosyl)-6-methoxy-9H-purine was tested as described above.

| $IC_{50}$ | |
|---|---|
| Inhibition of Reverse Transcriptase | |
| HIV-1 | HIV-2 |
| 9.5 $\mu$M | 3.2 $\mu$M | b) Antiviral Activity Against Hepatitis B Virus (HBV)

i) Determination of anti-HBV activity was carried out by testing the ability of a compound to prevent replication of duck HBV in vitro, in the manner described by Tuttleman, Pugh and Summers (J. Virol., 58:17-25, 1986). Duck hepatoytes were obtained and placed in culture, and infected with duck HBV. Three days after infection, the infected cells were exposed to various concentrations of the test compound for an additional period of eight days. After this exposure, DNA was extracted from each culture of infected cells and compound, and the amount of viral DNA was specifically determined and compared with that obtained from similar cultures lacking the test compound.

The compound of Example 2c, 2-amino-9-(3-azido-2,3-dideoxy-$\beta$-D-erythro-pentofuranosyl)-6-methoxy-9H-purine was tested as described above.

| Concentration ($\mu$M) | Total Single Stranded Viral DNA content (picograms) |
|---|---|
| 0.01 | 175 |
| 0.1 | 100 |
| 1.0 | 75 |
| 10 | 25 |
| 100 | 9 | ii) The human HBV producer cell line of HepG2, 2.2.15, described and characterized by Sells et al., PNAS 84:1005, 1987 and J. Virol. 62:2836, 1988, has been shown to share many characteristics of the HBV chronically infected hepatocyte. It is infectious as demonstrated by the ability to cause disease in chimpanzees. This cell line was utilized in vitro to identify compounds with anti-HBV activity.

To test compounds for antiviral activity, monolayer cultures were treated with compound. 50–200M, for ten days. Supernatant media containing extracellular virion DNA (Dane particles) were harvested on days three, six and ten, treated with proteinase K (1 mg/mL) and sodium dodecyl sulfate (1%), and incubated at 50° C. for one hour. DNA was extracted with equal volumes of phenol followed by chloroform and then precipitated by ammonium acetate and propanol. The DNA precipitate was dissolved and collected on nitrocellulose using the procedure of Schleicher and Schuell (S & S. 10 Optical Ave., Keene, NH 03431, Publication #700, 1987). and treated as described by Southern, J. Mol. Biol. 98:503, 1975. Cells were harvested, and the intracellular DNA was obtained after cell lysis with guanidine isothiocyanate. The intracellular DNA was handled in the same manner as the extracellular DNA. After precipitation by ammonium acetate and propanol, the intracellular DNA precipitate was dissolved, cut by restriction endonuclease, Hind III, applied to agarose gel and then treated as described by Southern to determine the quantity of replicative intermediate forms. The antiviral effect of the drug was determined by measuring at least a 100-fold reduction of the amount of Dane particles extruded into the culture medium and a similar decrease in the intracellular replicative intermediates.

The compound of 7b showed strong inhibition of human hepatitis B virus.

We claim:
1. The compound 2-amino-9-(3-azido-2,3-dideoxy-$\beta$-D-erythropentofuranosyl)-6-pyrrolidinyl-9H-purine.
2. A pharmaceutically acceptable salt of 2-amino-9-(3-azido-2,3-dideoxy-$\beta$-D-erythro-pentofuranosyl)-6-pyrrolidinyl-9H-purine.

* * * * *